United States Patent [19]

Larue

[11] Patent Number: 5,705,399
[45] Date of Patent: Jan. 6, 1998

[54] SENSOR AND METHOD FOR DETECTING PREDETERMINED CHEMICAL SPECIES IN SOLUTION

[75] Inventor: Rebecca A. Larue, Levittown, Pa.

[73] Assignee: The Cooper Union for Advancement of Science and Art, New York, N.Y.

[21] Appl. No.: 247,041

[22] Filed: May 20, 1994

[51] Int. Cl.$^6$ .................. G01N 33/543; G01N 33/551; G01N 33/552

[52] U.S. Cl. .................. 436/501; 73/61.75; 73/64.53; 73/579; 73/580; 310/311; 310/312; 310/313 R; 310/313 A; 310/340; 310/361; 310/365; 310/367; 310/369; 422/68.1; 422/82.01; 435/7.1; 435/283.1; 435/287.2; 436/518; 436/524; 436/525; 436/527

[58] Field of Search ................ 73/61.75, 64.53, 73/579, 580, 584, DIG. 4; 310/311, 312, 313 R, 313 A, 340, 361, 365, 367, 369; 422/50, 68.1, 82.01; 435/7.1, 287, 291, 287.1, 287.2; 436/500, 501, 518, 524, 525, 527, 531, 532, 149–151, 806, 807, 817

[56] References Cited

U.S. PATENT DOCUMENTS

| | | | |
|---|---|---|---|
| 3,853,467 | 12/1974 | Giaever | 424/12 |
| 3,879,992 | 4/1975 | Bartera | 310/8 |
| 4,242,096 | 12/1980 | Oliveira et al. | 422/57 |
| 4,314,821 | 2/1982 | Rice | 422/61 |
| 4,410,633 | 10/1983 | Hertl et al. | 436/500 |
| 4,644,804 | 2/1987 | Ramm et al. | 310/338 |
| 4,735,906 | 4/1988 | Bastiaans | 436/527 |
| 4,737,456 | 4/1988 | Weng et al. | 435/4 |
| 4,847,193 | 7/1989 | Richards et al. | 436/501 |
| 4,999,284 | 3/1991 | Ward et al. | 435/4 |
| 5,001,053 | 3/1991 | Takaishi et al. | 435/4 |
| 5,135,852 | 8/1992 | Ebersole et al. | 435/39 |
| 5,179,028 | 1/1993 | Vali et al. | 436/524 |
| 5,270,166 | 12/1993 | Parsons | 436/520 |
| 5,283,037 | 2/1994 | Baer et al. | 422/82.01 |
| 5,455,475 | 10/1995 | Josse et al. | 310/316 |

FOREIGN PATENT DOCUMENTS

| | | |
|---|---|---|
| 215669 | 3/1987 | European Pat. Off. |
| 3733986 | 4/1989 | Germany |
| WO8905977 | 6/1989 | WIPO |

OTHER PUBLICATIONS

H. Muramatsu et al., "Determination of microbes and immunoglobulins using a piezoelectric biosensor," in *Journal of Membrane Science*, vol. 41, pp. 281–290 (1989).

(List continued on next page.)

*Primary Examiner*—Christopher L. Chin
*Attorney, Agent, or Firm*—Brumbaugh, Graves, Donohue & Raymond

[57] ABSTRACT

A chemical sensor for measuring a change in the sensor mass relating to the interaction of a surface of the sensor with a solution comprises a crystal detector oscillator capable of providing a measurement signal based upon the resonant frequency of the crystal detector oscillator. The crystal detector oscillator has a first crystal side for directly contacting the solution, and a second crystal side isolated from contacting the solution. A first electrode is integral to the first crystal side, with the first electrode having an inner and outer perimeter defining an outer portion of the first crystal side which is exterior to the outer perimeter of the first electrode and an inner portion of the first crystal side which is interior to the inner perimeter of the first electrode. A second electrode is integral to the second crystal side. The sensor may be employed to detect the concentration of predetermined species in solution by adsorbing a predetermined species-specific complementary material such as an antibody onto the active crystal sites of the first crystal side, and thereafter contacting the first crystal side with the species-containing solution. The sensor may also be used to measure the change in sensor mass relating to the degradation of a coating applied to the first crystal side thereof.

56 Claims, 28 Drawing Sheets

OTHER PUBLICATIONS

B. Shao et al., "Determination of bovine haemoglobin by a piezoelectric crystal immunosensor," in *Fresenius Journal of Analytical Chemistry*, vol. 346, pp. 1022–1024 (Aug., 1993).

M. Minunni et al., "A piezoelectric quartz crystal biosensor as a direct affinity sensor," in *Analytical Letters*, vol. 27, pp. 1475–1487 (Aug., 1994).

M.D. Ward and D.A. Buttry, "In Situ Interfacial Mass Detection With Piezoelectric Transducers," in *Science*, vol. 249, pp. 1000–1006 (Aug. 31, 1990).

Brochure for Assay Procedure for Tetrabead–125 (Abbott Laboratories, Sep. 1988).

A. Ballato, T.J. Lukaszek and G.J. Iafrate, "Subtle Effects in High–Stability Quartz Resonators," pp. 337–373, in *Piezoelectricity* (Taylor and Gagnepain, eds.) (1985).

M.Y. Chan, Master's Thesis entitled "A Ring Electrode Quartz Crystal Microbalance For In Vitro Determination of Thyroxine Levels In Blood" (May, 1994).

Price Quotation for Elchema Electrochemical Quartz Crystal Nanobalance System EQCN–600–S (Apr. 28, 1993).

Elchema Invoice No. 0001049 (May 21, 1993).

Elchema Packing List No. 12658 (Jul. 16, 1993).

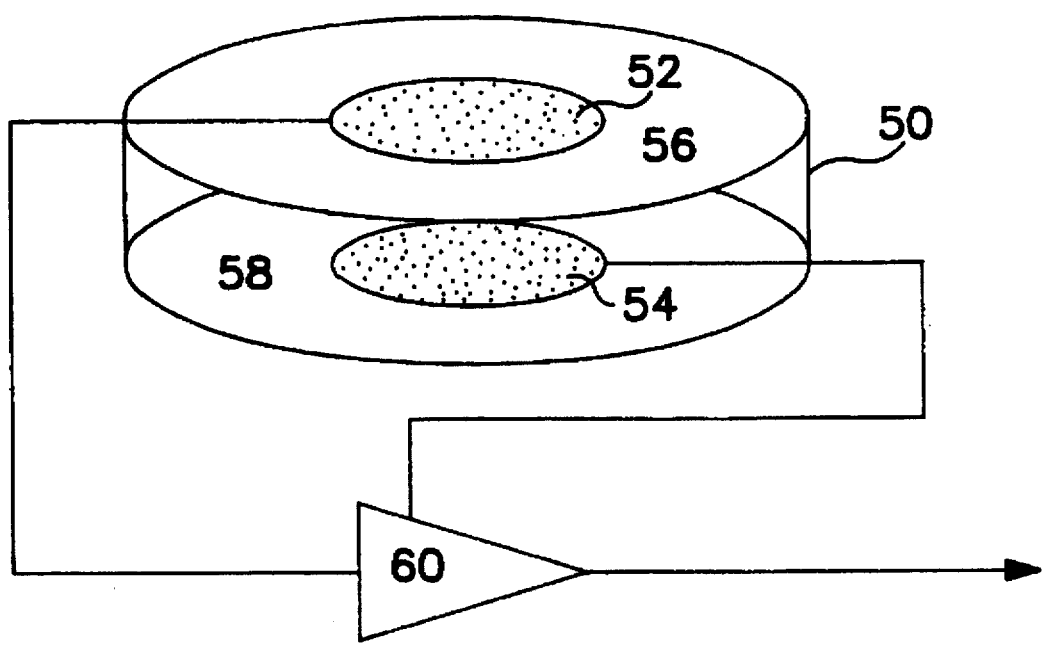
FIG. IA
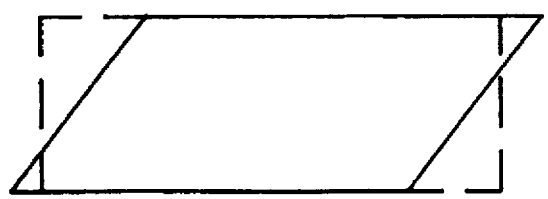
FIG. IB

```c
#include "c:\lw\include\formatio.h"
#include "c:\lw\include\lwsystem.h"
#include "c:\lw\include\userint.h"
#include "c:\lw\include\dataacq.h"
#include "c:\mike\thyrox\eqcn.h"
#include "c:\mike\thyrox\eqcnn.h"

#define SAVGSIZ 12
define AVGSIZ 12 int panel, menu, saved;
double timedata[DATASIZ];
long freqdata[DATASIZ];

/* calculates time difference: t2-t1 */
double duration(t1, t2)
double t1, t2;
{
double dur;
    if (t2 > t1)
        dur = t2 - t1;
    else
        dur = t2 - t1 + SECS_IN_DAY;
    return dur;
} main()
{
    char filename[80], msg80[80];
    int status, action, select, control, started, paused;
    int retval, pswitch, brd, timex, idx;
    long startfreq, fmem[AVGSIZ];
    double curtime, startime, lastrefresh;

panel = LoadPanel ("EQCN.UIR", EQCN);    /* get display panel */
    DisplayPanel (panel);                     /* display display panel */
    menu = LoadMenuBar ("EQCN.uir", MENU);   /* display menu bar */
    Init_DA_Brds (BRDSLOT, &brd);   /* initialize DA board */
    /* Configure Digital Port C (2) */
    /* no-handshaking mode (0), and for output (1) */
    DIG_Prt_Config(BRDSLOT, PORTC, 0, 1);
    /* set up ctr 80, initially high */
    /* Mode 3: square wave generator,
    /* PERIOD counts bet. outputs (Internal clock Freq/PERIOD) */
    /* binary counter */
    ICTR_Reset(BRDSLOT, 0, 1);
    ICTR_Setup(BRDSLOT, 0, 3, PERIOD, BINBCD);
```

FIG. 18A

```
timex=0;                          /* data array index */
saved=0;
idx=0;                            /* data # count */
started=FALSE;                    /* hasn't started yet */
status = PAUSING;                 /* status: waiting to start */
paused = FALSE;                   /* pause key not pressed */
lastrefresh=timer();
Fmt(filename, "blank.txt");       /* default filename */
while (status != QUITTING)        /* while pwr not turned off */
{
    if (started==FALSE)
        curtime=0.0;
else
    curtime=duration(startime,timer());
PrintStatus(status, curtime);
action=GetUserEvent (0, &select, &control);
if (status==RECORDING)
{
    GetData(&fmem[idx], status);
    idx=idx+1;
    if ((idx%AVGSIZ) == 0)
    {
        idx=0;
        FindAvgFreq(&freqdata[timex], fmem);/* avg filter & store */
        timedata[timex]=curtime/60.0;    /* convert to min */
        PlotStripChart(panel, EQCN_FREQGRAPH, freqdata, 1, timex, 0, 2);
        timex = timex + 1;
        if (saved == 0)                  /* set startfrequency */
            startfreq = freqdata[0];
    }
    if (timex >= DATASIZ)
    {
        SaveFile(filename, &timex);
    }
}   /* if recording */
else
{   /* if no activity for more than 1 min */
    if (duration(lastrefresh, timer()) >= 60.0)
    {
        Blanks(panel);                   /* Refresh Graphs to save mem */
        lastrefresh=timer();             /* reset lastrefresh time */
    }
}
if (action && select==panel)
{
    switch (control)
    {
```

FIG. 18B

```
case EQCN_POWER:
    GetCtrlVal(panel, EQCN_POWER, &pswitch);
    SetCtrlVal(panel, EQCN_PLIGHT, pswitch);
    if ((pswitch) && (started==FALSE))
    {
        started=TRUE;
        paused=FALSE;
        startime=timer();
        status=RECORDING;
    }
    else
    {
        status=QUITTING;
        SaveFile(filename,&timex);
    }
    break;
case EQCN_PAUSE:
    if ((status == PAUSING) && (started == TRUE))
        status=RECORDING;
    else
        status=PAUSING;
    break;
case EQCN_RESETBUTTON:
    if (ConfirmPopup("Do you REALLY want to RESET/Start Over?"))
    {
            SaveFile(filename, &timex);
            SetCtrlVal(panel, EQCN_POWER, 0);
            SetCtrlVal(panel, EQCN_PLIGHT, 0);
            saved=0;
            idx=0;                      /* data # count */
            started=FALSE;              /* hasn't started yet */
            status = PAUSING;           /* status: waiting to start */
            Fmt(filename, "blank.txt"); /* default filename */
            paused=FALSE;
            Blanks(panel);
    }
        break;
    case EQCN_ENTER:
            PatInfo(filename);
        break;
    case EQCN_UPDATE:
            UpdateStat(startfreq, timex);
        break;
    case EQCN_HELP:
        break;
    } /* select panel switch */
} /* if select */
```

FIG. 18C

```
if (action && select==menu)
{
    switch (control)
    {
        case MENU_FILE_SAVE:
                GetFileName("Opening File To Save",filename);
                SaveFile(filename, &timex);
                Fmt(msg80,"%s<File %s saved.",filename);
                MessagePopup(msg80);
            break;
        case MENU_FILE_SAVEFILE:
                SaveFile(filename, &timex);
            break;
        case MENU_FILE_START:
                if (started == FALSE)
                {
                    SetCtrlVal(panel, EQCN_POWER, 1);
                    SetCtrlVal(panel, EQCN_PLIGHT, 1);
                    started=TRUE;
                    paused=FALSE;
                    startime=timer();
                    status=RECORDING;
                }
            break;
        case MENU_FILE_QUIT:
                status=QUITTING;
                SaveFile(filename,&timex);
            break;
        case MENU_FILE_QUITNS:     /* Quit w/o Save */
                status=QUITTING;
            break;
        case MENU_CTRL_PAUSE:
                if ((status == PAUSING) && (started == TRUE))
                    status=RECORDING;
                else
                    status=PAUSING;
            break;
            case MENU_CTRL_UPDATE:
                    UpdateStat(startfreq, timex);
                break;
            case MENU_CTRL_ENTER:
                    PatInfo(filename);
                break;
            case MENU_CTRL_RESET:
                    if (ConfirmPopup("Do you REALLY want to RESET/Start Over?"))
                    {
```

FIG. 18D

```
                    SaveFile(filename, &timex);
                    SetCtrlVal(panel, EOCN_POWER, 0);
                    SetCtrlVal(panel, EOCN_PLIGHT, 0);
                    saved=0;
                    idx=0;                          /* data # count */
                    started=FALSE;                  /* hasn't started yet */
                    status = PAUSING;               /* status: waiting to start */
                    Fmt(filename, "blank.txt");     /* default filename */
                    paused=FALSE;
                    Blanks(panel);
                    }
                break;
            case MENU_HELP_ABOUT:
                break;
            case MENU_HELP_GENERAL:
                break;
            case MENU_HELP_PAUSE:
                break;
            case MENU_HELP_UPDATE:
                break;
            case MENU_HELP_SAVE:
                break;
            case MENU_HELP_RESET:
                break;
            } /* select menu switch */
        } /* if menu switch */
    } /* While */
} /*main*/
/* Average filtering frequency readings */
int findAvgFreq(favg, freq)
long freq[AVGSIZ], *favg;
{
long tmp;
int i, avgct;
    tmp=0;
    avgct=AVGSIZ;
    for (i=AVGSIZ-avgct; i<AVGSIZ; i++)
        tmp+=freq[i]/avgct;
    *favg=tmp;
    return 0;
}
/* read count from counter B[ctrn], save it in lct */
long ReadCtr(ctrn, lct)
int ctrn;
long *lct;
{
int rt, ct;
    rt=ICTR_Read(BRDSLOT, ctrn, lct);
```

FIG. 18E

```
    if (ct < 0)
        *lct=ct+65536;
    if (rt==0)
        return *lct;
    else
        return *lct;
} long FindSAvgFreq(freq)
long freq[SAVGSIZ];
{
long tmp;
int i, j, avgct;
    for (i=0; i<SAVGSIZ-1; i++)
        for (j=0; j<SAVGSIZ-1; j++)
            if (freq[j] > freq[j+1])
            {
                tmp=freq[j];
                freq[j]=freq[j+1];
                freq[j+1]=tmp;
            }
    tmp=0;
    avgct=SAVGSIZ/4;
    for (i=SAVGSIZ-avgct; i<SAVGSIZ; i++)
        tmp+=freq[i]/avgct;
    return tmp;
}

/* convert freq. change to mass change, using Sab's eqn */
double MassConvert(long delf)
{
double ug;
    delf = delf/1000.0;    /* convert reading to kHz */
    ug=KONST*delf;
    return ug;
}

/* Get frequency reading using 3 counters */
int GetData(freq, st)
int st;
long *freq;
{
int i, rt;
long ct0, ct1, frequency, sf[SAVGSIZ];
double mass;
char msg[80];
```

FIG. 18F

```c
if (!(st & RECORDING))
    return st;

for (i=0; i<SAVGSIZ; i++)
{
    /* setup counter B1 & B2, initially high, start at STARTCT and ct down */
    /*     mode 0: gate triggered (ctrlled by port C), binary */
    /* B2 clocked from B0, B1 clocked from external frequency input */
    rt=ICTR_Reset(BRDSLOT, 2, 1);
    rt=ICTR_Setup(BRDSLOT, 2, 0, 0, BINBCD);
    rt=ICTR_Reset(BRDSLOT, 1, 1);
    rt=ICTR_Setup(BRDSLOT, 1, 0, 0, BINBCD);

/* start counters: write 1 to output port C */
        DIG_Out_Port(BRDSLOT, PORTC, 1);
        for (rt=0; rt<DELAY; rt++);        /* counting down (delay) */
        DIG_Out_Port(BRDSLOT, PORTC, 0);   /* write 0: stop counting */
        ct1=STARTCT-ReadCtr(1, &ct1);      /* find count from B1 */
        ct0=STARTCT-ReadCtr(2, &ct0);      /* find count from B2 */ sf[i]=ct1*((CTRCLK/PERIOD)/ct0);   /* convert to frequency */
}
frequency=FindSAvgFreq(sf);
mass = MassConvert(frequency);            /* convert to mass deposit reading */
Fmt(msg, "%s<----%i[b4] Hz----",frequency); /* show readings */
PlotText(panel, EQCM_FREQ, 0.0, 0.0, msg, SYSTEM, WHITE, BLUE);
Fmt(msg, "%s<----%f[p1] ug----",mass);
PlotText(panel, EQCM_MASS, 0.0, 0.0, msg, SYSTEM, WHITE, BLUE);
*freq=frequency;
return st;
}

/* print experiment run time and status of experiment */
int PrintStatus(stat, timenow)
double timenow;
int stat;
{
char statmsg[80], msg2[80];

switch (stat)
    {
        case PAUSING:
                Fmt(statmsg,"%s<-----PAUSING-----");
            break;
        case RECORDING:
                Fmt(statmsg,"%s<----RECORDING----");
            break;
    }
```

FIG. 18G

```
        PlotText(panel, EQCN_STATWINDOW, 0.0, 1.0, statmsg, SYSTEM, WHITE, CYAN);
        Fmt(msg2,"%s<    Time: %f[p2] min         -", timenow/60.0);
        PlotText(panel, EQCN_STATWINDOW, 0.0, 0.0, msg2, BOS15, RED, CYAN);
} int GetFileName(title,filename)
char *title,*filename;
{
char dirname[80];

GetProgramDir (dirname);
   if (FileSelectPopup (dirname, "*.txt", title , 0, 1, 1, filename) != 1)
     return;
}

/* save file with known file name */
int SaveFile(char fname[80], int *maxtime)
{
int fd;
int index;

fd = OpenFile (fname, FILE_WRITE, FILE_APPEND, FILE_ASCII);
     for (index=0; index<*maxtime; index++)
     {

FmtFile (fd, "%s<%f[p2w15]       %i[b4] ",
                timedata[index], freqdata[index]);
        WriteFile(fd,"\n",1);
     }
     CloseFile (fd);
     *maxtime=0;
     saved=saved+1;
     return 0;
} int PatInfo(char fname[80])
{
char prompt[80], response[20], lname[80], frname[80], idstr[80];
int fd;

DeletePlots(panel, EQCN_PATINFO);

/* Get Patient Info */
     Fmt(prompt, "Input Patient Last Name: ");
     PromptPopup(prompt, response, 15);
     Fmt(lname,"%s<Last Name: %s", response);
```

FIG. 18H

```
Fmt(prompt, "Input Patient First Name: ");
PromptPopup(prompt, response, 15);
Fmt(frname,"%s<First Name: %s", response);

Fmt(prompt, "Input Patient ID#: ");
PromptPopup(prompt, response, 15);
Fmt(idstr,"%s<ID Number: %s", response);

Fmt(prompt, "Input File Name: ");
PromptPopup(prompt, fname, 15);

/* display patient info on screen */
PlotText(panel, EQCN_PATINFO, 2.0, 75.0, lname, CHI15, BLACK, GRAY);
PlotText(panel, EQCN_PATINFO, 2.0, 45.0, frname, CHI15, BLACK, GRAY);
PlotText(panel, EQCN_PATINFO, 2.0, 15.0, idstr, CHI15, BLACK, GRAY);

/* write patient info to file */
fd = OpenFile (fname, FILE_WRITE, FILE_TRUNC, FILE_ASCII);
FmtFile (fd, "%s<%s \n", lname);
FmtFile (fd, "%s<%s \n", frname);
FmtFile (fd, "%s<%s \n", idstr);
CloseFile (fd);
return 0;
}

/* Show Stat: freq. change from start to current, elapsed time */
int UpdateStat(long stfreq, int tx)
{
char line1[80], line2[80], line3[80], line4[80];

if (tx > 0)
        tx=tx-1;
    Fmt(line1, "%s< Initial Frequency Reading: %i[b4] Hz     ",stfreq);
    Fmt(line2, "%s< Updated Frequency Reading: %i[b4] Hz     ",freqdata[tx]);
    Fmt(line3, "%s< Change in Frequency Reading: %i[b4] Hz   ",stfreq-freqdata[tx]);
    Fmt(line4, "%s< Elapsed Time: %f[p2] min                 ",timedata[tx]);

PlotText(panel, EQCN_STAT, 2.0, 86.0, line1, CHI15, BLUE, CYAN);
    PlotText(panel, EQCN_STAT, 2.0, 59.0, line2, CHI15, BLUE, CYAN);
    PlotText(panel, EQCN_STAT, 2.0, 32.0, line3, CHI15, BLUE, CYAN);
    PlotText(panel, EQCN_STAT, 2.0, 5.0, line4, CHI15, BLUE, CYAN);
    return 0;
}

/* Blanks all windows */
int Blanks(int panel)
{
```

FIG. 18I

```
        DeletePlots(panel, EQCM_STAT);
        DeletePlots(panel, EQCM_PATINFO);
        DeletePlots(panel, EQCM_FREQ);
        DeletePlots(panel, EQCM_MASS);
        DeletePlots(panel, EQCM_FREQGRAPH);
        DeletePlots(panel, EQCM_STATWINDOW);

return 0;
}
/* LabWindows User Interface Resource (UIR) Include file         */
/* Copyright (c) National Instruments 1992. All Rights Reserved. */

/* WARNING: Do not add to, delete from, or otherwise modify the contents */
/*          of this include file.                                        */
#define MENU 0
#define MENU_FILE 0
#define MENU_FILE_SAVEFILE 1
#define MENU_FILE_SAVE 2
#define MENU_FILE_START 3
#define MENU_FILE_QUIT 4
#define MENU_FILE_QUITWS 5
#define MENU_CTRL 256
#define MENU_CTRL_PAUSE 257
#define MENU_CTRL_UPDATE 258
#define MENU_CTRL_ENTER 259
#define MENU_CTRL_RESET 260
#define MENU_HELP 512
#define MENU_HELP_ABOUT 513
#define MENU_HELP_GENERAL 514
#define MENU_HELP_PAUSE 515
#define MENU_HELP_UPDATE 516
#define MENU_HELP_SAVE 517
define MENU_HELP_RESET 518 define EQCM 0
define EQCM_FREQGRAPH 0
#define EQCM_FREQ 1
#define EQCM_PLIGHT 2
#define EQCM_POWER 3
#define EQCM_STATWINDOW 4
#define EQCM_RESETBUTTON 5
#define EQCM_MASS 6
#define EQCM_PAUSE 7
#define EQCM_ENTER 8
#define EQCM_UPDATE 9
#define EQCM_HELP 10
#define EQCM_PATINFO 11
#define EQCM_STAT 12
```

FIG. 18J

```
/* definitions for eqcn.c */
/* #define AVGSIZ 50 */
#define PORTC 2
#define STARTCT 65536
#define DELAY 5000
#define CTRCLK 2000000   /* counter 0 clock at 2 MHz */
#define DATASIZ 50
#define SECS_IN_DAY 86400.0
#define FREQRES 10000.0   /* Res Freq of 10 MHz (10000 KHz) */
#define KONST 0.8325885   /* constant in formula (4 sig dig) in mg/kHz */
#define TRUE   1
#define FALSE  0
#define BRDSLOT 1
#define BINBCD 1
#define PERIOD 20
#define BLACK 0
#define BLUE 1
#define GREEN 2
#define CYAN 3
#define RED 4
#define MAGENTA 5
#define BROWN 6
#define GRAY 7
#define HGRAY 8
#define HBLUE 9
#define HGREEN 10
#define HCYAN 11
#define HRED 12
#define HMAGENTA 13
#define YELLOW 14
#define WHITE 15
#define SYSTEM 0
#define BOS15 5
#define BOS24 6
#define LED20 12
#define SEG7 14
#define CHI15 9
#define CHI24 10
#define FILE_READ 1
#define FILE_WRITE 2
#define FILE_APPEND 1
#define FILE_TRUNC 0
#define FILE_ASCII 1
#define FILE_BINARY 0
#define READERR 0
#define QUITTING 0
#define PAUSING 1
#define RECORDING 2
```

FIG. 18K

SENSOR AND METHOD FOR DETECTING PREDETERMINED CHEMICAL SPECIES IN SOLUTION

BACKGROUND OF THE INVENTION

This invention relates to a chemical sensor for measuring a change in the sensor mass relating to the interaction of a surface of the sensor with a solution, an apparatus which comprises the sensor, a method for using the sensor, and a method for using the apparatus.

The necessity for the quantitative determination of various chemical species in solution is well known. For example, the necessity of quantitative determination of antigen presence, hormonal concentration, HIV activity, etc. in human blood or other body fluids to aid in the diagnosis and treatment of various illnesses is well known. In addition, the necessity of determining concentrations of various pollutants and toxic substances for environmental monitoring, toxicological studies, etc. is well known. Conventional methods previously employed for such quantitative analyses include radioimmunoassay (RIA), molecular fluorescence techniques, and precipitation reactions.

However, such methods all have attendant disadvantages. RIA typically require hazardous radioactive materials. Molecular fluorescence techniques are imprecise and may be impractical for concentration determinations of certain chemical species. Wet chemical analytical techniques such as precipitation reactions may require various instable and strongly temperature, pH and time dependent reagents. In addition, such techniques are often time-consuming and difficult, and require a sophisticated analytical laboratory environment.

Jacques and Pierre Curie in 1880 experimentally showed that mechanical stress applied to the surface of a quartz crystal induced an electrical potential across the crystal whose magnitude was proportional to the applied stress. This phenomenon is referred to as the piezoelectric effect. The charges that are generated in the quartz crystal are due to the formation of dipoles that result from the displacement of atoms in the acentric crystalline lattice. This electric polarization produced by mechanical stress is termed the direct piezoelectric effect. Closely related to this is the converse piezoelectric effect, which Walter Cady demonstrated in the 1920's. He observed that the application of a voltage across a quartz crystal affords a corresponding mechanical strain, and concluded that this knowledge could be utilized in the construction of very stable oscillator circuits. In the oscillator, the application of an alternating electric field (AC) across a quartz crystal substrate results in an alternating strain field. In fact, quartz crystals have been shown to vibrate with very little energy dissipation; as such they are nearly perfect oscillators. These factors coupled with their low cost, ruggedness, low defect aspect, facile fabrication, and chemical inertness have resulted in their widespread use in frequency control and filter circuits.

The electromechanical coupling and stresses that result from applied electric fields depend on the angle of symmetry, angle of cut of the crystal substrate, and the configuration of the excitation electrodes used to apply the electric field across the crystal. A preferred type of crystal for use as a piezoelectric oscillator is an AT-cut quartz crystal. It is obtained by cutting wafers of quartz at approximately 35° from the z-axis. By applying an alternating field across the thickness of the AT-cut quartz, by two electrodes on opposite sides of the crystal, shear vibrations can be obtained in the x-axis direction parallel to the electric field and propagation of a transverse shear wave through the crystal in the thickness direction is caused. This is illustrated in FIG. 1A. In FIG. 1, an AT-cut quartz crystal 50 has disk-shaped electrodes 52 and 54 on crystal surfaces 56 and 58 respectively. The electrodes are operatively coupled to means 60 for measuring the resonant frequency of the crystal. The illustration of FIG. 1B depicts a cross-sectional view of the crystal and shows the direction that the quartz surface vibrates. The mode of vibration is termed thickness shear.

The role of the piezoelectric effect in mass detection is readily explained using the example of the thickness-shear mode exhibited by AT-cut quartz crystals. The electric field, and therefore the piezoelectric strain and vibration of the quartz crystal, is essentially confined to the area between two excitation electrodes. The shear motion that results is directly analogous to transverse waves traveling in a string of length L bound at both ends, where standing waves can result provided their wavelengths are integral divisors of 2L. A resonant condition with standing waves is satisfied when the string is driven by impulses at a frequency matching the fundamental or one of the harmonic frequencies. The fundamental frequency, $f_0$, of the string is:

$$f_0 = \frac{\sqrt{\frac{S}{m_1}}}{2L} \tag{I}$$

where S is the tension on the string and $m_1$ is the mass per unit length. An increase in $m_1$ results in a decrease in $f_o$. For example, the violin has thinner strings than a base viol, hence a higher fundamental frequency.

In the case of the fundamental shear mode of an AT-cut quartz crystal:

$$f_0 = \frac{\sqrt{\frac{\mu}{\rho}}}{2t_q} \tag{II}$$

where $\mu$ and $\rho$ are the shear modulus ($2.947 \times 10^{11}$ dyne/cm$^2$) and density (2.648 g/cm$^3$) of quartz, respectively. Increasing the quartz thickness, $t_q$, results in a decrease in the fundamental frequency.

Sauerbrey showed experimentally, in 1957, that foreign layers deposited on thickness-shear mode crystals reflect the mass-frequency relation in equation II. His mass-sensing format is commonly referred to as the quartz crystal microbalance (QCM). The derivation of his mass-frequency relation relies on the assumption that a deposited foreign material exists entirely at the antinode of the standing wave propagating across the thickness of the quartz crystal, so that the foreign deposit could be treated as an extension of the quartz crystal. Therefore, the frequency change is calculated as though it were the result of an increase in thickness of the quartz crystal:

$$\frac{\Delta f}{f_0} = -\frac{\Delta t}{t_q} \tag{III}$$

By making appropriate substitutions to the terms on the left side of equation III, the resulting equation is in the desired form of:

$$\Delta f = \frac{-2f_0^2 \Delta m}{A} \tag{IV}$$

where $\Delta f$ is the frequency shift, in Hz, associated with the given mass change, $f_0$ is the fundamental operating frequency of the device, in MHz, $\Delta m$ is the change in mass on the surface of the crystal, in grams, and A is the surface area of the device, in cm$^2$.

Chemical sensors which achieve detection of chemical species via the piezoelectric effect are advantageous over many of the foregoing methods, and are also known in the art. For example, the use of QCM systems, in which changes in the vibrational resonant frequency of piezoelectric quartz crystal oscillators are employed to measure concentrations of chemical species, are generally discussed by M.D. Ward and D.A. Buttry in "In Situ Interfacial Mass Detection with Piezoelectric Transducers" in Science, Vol. 249, pp. 1000–1006 (1990). The mathematical algorithms necessary to convert the resonant frequency of an antigen or antibody coated oscillator to a concentration measurement of chemical species in solution are set forth in U.S. Pat. No. 5,001,053 (Takahashi et al.), incorporated herein by reference. U.S. Pat. No. 4,735,906 (Bastiaans) discloses the use of a pair of piezoelectric crystal sensors to detect and measure the amount of antigen or antibody in a test solution. One sensor serves as a reference sensor and the second sensor has its surface modified by bonding a silane derivative to the surface, and then binding the antigen or antibody to the resultant siloxane polymer. Measurement of the resonant frequencies of the sensors using surface acoustic waves (SAW) yields the concentration of antibody or antigen in the test solution. However, sensors employing SAW devices are disadvantageous for use in determining the concentration of chemical species in liquids (e.g. human blood), as discussed, for example, by Ward and Buttry. In addition, the use of chemical bonding agents on the crystal surface is disadvantageous, as it introduces a source of error which may distort measurement of the crystal's resonant frequency. In addition, U.S. Pat. No. 4,242,096 (Oliveira et al.) discloses the use of a piezoelectric oscillator to detect antigens, in which the antigen is immobilized on the oscillator, and an antibody for the antigen is also contacted with the liquid sample containing the antigen. The piezoelectric oscillator employed uses disk-shaped electrodes on both faces which cover a major portion of the oscillator surface, thereby disadvantageously preventing the majority of the active crystal sites from direct contact with the antigen.

Home and Alberti have investigated many aspects concerning biosensors in medicine and the corresponding requirements from medical practitioners. They describe laboratory bias, in terms of the increased demand during this century, for more sophisticated and automated analytical devices. The rise of chemical pathology and clinical biochemistry is attributed to the pressure of increased clinical demand. What this leads to, however, is a batch processing of laboratory orders and a decrease in the flexibility of service and, in addition, takes away from local hospital services at small institutions in favor of major installations in metropolitan areas.

They allude to a number of trends that have developed in recent decades that may skew routine laboratory work towards a clinical setting. It is well documented that patients in intensive care units show expeditious fluctuations in biochemical variables and, therefore, require timely and rapid recognition of problems and immediate remediation. At first, small sections of hospitals were converted into biochemical measurement wards utilizing basic analytical assays. Later, the development of single specimen instruments gave quick results for measurements of blood gases, potassium levels and glucose concentrations. A second area of concern are the economic factors involved with increasingly expensive patient diagnoses.

Surveys of hospitals and doctors have shown an increase in dissatisfaction with having to examine a problem, enact investigations, and then later having to reassess the problem at a later time in light of the results from the investigations. The patients are also pleased with rapid remediation of their cases. As such, the ability to perform a variety of important analyses relating to quantitative determination of predetermined chemical species in blood, etc. in a doctors office or a hospital out-patient clinic is an important feature of this invention.

In view of the foregoing, it would be advantageous in the measurement of a change in sensor mass relating to the interaction of a surface of the sensor with a solution, such as in the measurement of the degradation of a coating applied to the sensor or in the measurement of predetermined chemical species in solution, to employ a piezoelectric oscillator chemical detector which avoids the use of chemical bonding agents at the crystal surface, avoids the use of SAW devices, and enables a major portion of the oscillator crystal surface to be used for coating with a species-specific complementary material to detect the presence of the corresponding chemical species. It would also be advantageous to employ a detector and method which are readily useable in a clinical setting.

It is one object of this invention to provide a chemical sensor for measuring a change in the sensor mass relating to the interaction of a surface of the sensor with a solution which avoids the use of chemical bonding agents at the crystal surface, avoids the use of SAW devices and their attendant problems, and enables a major portion of the oscillator crystal surface to be made available for adsorption of materials such as coatings or predetermined chemical species.

It is one feature of this sensor that it comprises a crystal detector oscillator which has a first electrode integral to the first side of the crystal which contacts the coating or species-containing solution. The first electrode has an inner and outer perimeter defining an outer portion of the first crystal side which is exterior to the outer perimeter of the first electrode and an inner portion of the first crystal side which is interior to the inner perimeter of the first electrode, thereby advantageously defining active crystal sites on the surface of the first crystal side both interior and exterior to the electrode. The crystal detector oscillator also has a second side which is isolated from contacting the coating or species-containing solution, and which contains a second electrode integral to the second crystal side.

It is another feature of this invention that a coating may be applied to the first crystal side and a change in the sensor mass relating to degradation of the coating is measured.

It is another feature of this invention that the first crystal side may be contacted with a solution containing a predetermined species-specific complementary material (e.g. an antibody) prior to contacting the first crystal side with the species-containing solution. The molecules of the complementary material thus orient to the active crystal sites both interior and exterior to the first electrode. When the first crystal side is contacted with the species-containing solution (e.g. a solution containing an antigen (i.e. the species) specific to the antibody), the species molecules adsorb onto the molecules of the complementary material residing on the first crystal side active sites. By advantageously employing an electrode having an outer and inner perimeter on the first crystal side, additional active crystal sites located in the interior portion of the ring are available for adsorbing the specific complementary material and predetermined species from solution.

The sensor of this invention advantageously provides a highly accurate device for measuring, for example, the degradation of a coating applied to the first crystal side or the concentration of predetermined species in solution, and provides a more sensitive detector with a lower detection limit than conventional sensors having electrode surfaces contacting a species-containing solution. The sensor advantageously achieves rapid measurements of species in solution (e.g. under half an hour), is inexpensive in comparison with techniques such as RIA, and does not require the extensive operator training typically associated with wet chemistry and other technical assays used in analytical laboratories. The sensor is also advantageously reusable after employing a simple cleaning procedure to remove adsorbed complementary material and species.

It is another object of this invention to provide an apparatus for measuring the change in sensor mass associated with the degradation of a coating which has previously been adsorbed onto the first crystal side of the sensor.

It is another object of this invention to provide a method for detecting the concentration of predetermined chemical species in solution using the sensor of this invention. It is one feature of this method that the sensor is first contacted with a solution containing the complementary material, wherein the complementary material is specific for the predetermined chemical species to be detected. After the resonant frequency of the complementary material-adsorbed sensor is measured, the sensor is contacted with the species-containing solution, and molecules of the predetermined species are adsorbed onto molecules of the complementary material previously adsorbed onto the active crystal sites. The resonant frequency of the sensor is again measured, with the difference between the complementary material-adsorbed sensor frequency and complementary material plus species-adsorbed sensor frequency being indicative of the concentration of species in solution. It is another feature of this invention that a reference crystal oscillator having a reference resonant frequency may also be employed to normalize the sensor frequency values obtained, thereby eliminating various sources of error associated with such measurements. The method of this invention is advantageously simple and yields highly accurate and repeatable results. In addition, as the sensor is easily cleaned for reuse, the method of this invention is advantageously useful when dealing with multiple samples such as blood samples from patients.

It is yet another object of this invention to provide an apparatus for detecting the concentration of a predetermined chemical species in solution. It is one feature of this apparatus that it comprises the chemical sensor of this invention operatively coupled to sensor detecting means which detect the resonant frequency of the crystal detector oscillator and provide a detector output signal representative of the crystal detector oscillator resonant frequency. It is another feature of this apparatus that the sensor detecting means may be operatively coupled to display means to display the species concentrations measured on a real-time or other basis for patient monitoring and the like. It is another feature of the apparatus that it may additionally employ a reference oscillator and detecting means operatively coupled to the reference oscillator for detecting the resonant frequency of the reference oscillator and providing a reference output signal representative of the reference oscillator resonant frequency. The reference oscillator resonant frequency may be used to normalize the sensor frequency values obtained, thereby eliminating various sources of error associated with such measurements. The apparatus yields highly accurate and repeatable results. In addition, the apparatus is relatively simple to use, with less training and expertise required than for other analytical techniques.

It is yet another object of this invention to provide a method for detecting the concentration of predetermined chemical species in solution using the apparatus of this invention. It is one feature of this method that the sensor is employed as described herein to obtain a measurement signal characteristic of the frequency of the complementary material-adsorbed sensor and the complementary material plus species-adsorbed sensor, and that sensor detecting means are employed to convert the measurement signal to a detector output signal. Display means operatively connected to the sensor detecting means advantageously display the data obtained from the apparatus.

SUMMARY OF THE INVENTION

The chemical sensor of this invention comprises a crystal detector oscillator capable of providing a measurement signal based upon the resonant frequency of the crystal detector oscillator. The crystal detector oscillator has a first crystal side for contacting a solution, and a second crystal side isolated from contacting the solution. A first electrode is integral to the first crystal side, with the first electrode shaped in such a manner (e.g. ring-shaped) as to define an outer portion of the first crystal side which is exterior to the outer perimeter of the first electrode and an inner portion of the first crystal side which is interior to the inner perimeter of the first electrode. A second electrode is integral to the second crystal side. The crystal detector oscillator is preferably a quartz crystal such as AT-cut quartz crystal. In one embodiment, a coating is adsorbed onto the first crystal side surface, and the change in sensor mass due to degradation of the coating may be measured. In another embodiment, a species-specific complementary material (e.g. a species-specific antibody such as anti-thyroxine) is adsorbed onto the active crystal sites of the first crystal side, and the first crystal side is thereafter contacted with the species-containing solution (e.g. a solution containing an antibody-specific antigen such as a human blood sample containing thyroxine), thereby causing adsorption of molecules of the predetermined species onto the complementary material-adsorbed active crystal sites. The difference in the measured resonant frequencies of the complementary material-adsorbed sensor and the complementary material plus species adsorbed sensor is indicative of and may be correlated with the concentration of the predetermined species in solution.

The method of using the sensor comprises, in a preferred embodiment, contacting the first crystal side of the chemical sensor with a solution containing a complementary material to the predetermined chemical species (e.g. an antibody specific to a predetermined antigen such as the antibody anti-thyroxine, which is specific to the antigen thyroxine), and measuring the resonant frequency of the crystal detector oscillator after contacting with the complementary material-containing solution. The first crystal side is thereafter contacted with a solution containing the predetermined chemical species (e.g. the antigen), and the resonant frequency of the crystal detector oscillator after contacting the first crystal side with the species-containing solution (e.g. a human blood sample containing thyroxine) is measured. The difference in resonant frequencies between the complementary material-adsorbed sensor and complementary material plus species adsorbed sensor is measured to determine the concentration of the species in the species-containing solution. A reference oscillator having a reference resonant frequency may also be employed to normalize the detector resonant frequency values measured, thereby eliminating various sources of error such as power fluctuations and the like. The reference oscillator may also be a crystal oscillator such as a quartz crystal.

The apparatus comprises the chemical sensor operatively coupled to sensor detecting means for detecting the resonant frequency of the crystal detector oscillator and providing a detector output signal representative of the crystal detector oscillator resonant frequency. The apparatus may additionally comprise display means operatively coupled to the sensor detecting means for displaying the detector output signal. In a preferred embodiment, the apparatus additionally comprises interface means operatively coupled to the sensor detecting means for converting the data output signal into a displayable form, and display means such as a computer terminal operatively coupled to the interface means for displaying the data output signal in a readily usable format. A reference oscillator and reference detecting means operatively connected thereto and capable of providing a reference output signal representative of the resonant frequency of the reference oscillator may also be used in conjunction with the apparatus, to normalize the detector frequency values measured. In this embodiment, signal comparison means operatively coupled to the sensor detecting means and reference detecting means are employed to compare the difference between the detector output signal and reference output signal and providing a difference output signal. The difference output signal can be relayed to display means for converting the difference output signal into a displayable form. The method of using the apparatus comprises employing the detector as described to obtain a detector output signal which may then be transmitted to display means for visual display.

This invention is particularly useful for measuring the concentration of various predetermined chemical species in solution. More particularly, in a preferred embodiment the invention may be employed to measure the concentration of various species such as thyroxine or calcitonin in human blood. The sensor provides a more sensitive detector with a lower detector limit than conventional sensors. The sensor also is advantageously easily cleaned and thus reusable, thereby making the sensor, apparatus and method of this invention particularly advantageous for use in a variety of settings such as hospitals, clinics, physician's offices and the like.

BRIEF DESCRIPTION OF THE DRAWINGS

FIG. 1A depicts a typical piezoelectric AT-cut quartz crystal.

FIG. 1B depicts an illustration of the vibrational movement of a typical piezoelectric AT-cut quartz crystal.

FIGS. 18A—18K set forth a complete program listing of the software employed in a preferred embodiment of this invention.

DETAILED DESCRIPTION OF THE INVENTION

Figure 2A:
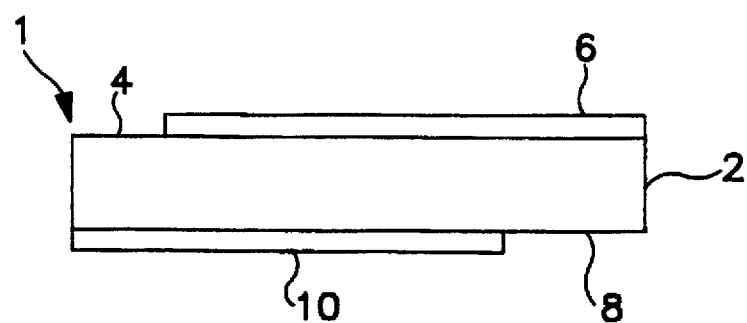
FIG. 2A depicts a side view of a preferred embodiment of the chemical sensor of this invention.

The chemical sensor of this invention comprises a crystal detector oscillator capable of providing a measurement signal based upon the resonant frequency of the crystal detector oscillator. The crystal detector oscillator has a first crystal side for contacting a solution, and a second crystal side isolated from contacting the solution. The crystal detector oscillator is preferably a quartz crystal, most preferably an AT-cut quartz crystal.

A first electrode is integral to the first crystal side, with the first electrode having an inner and outer perimeter defining an outer portion of the first crystal side which is exterior to the outer perimeter of the first electrode and an inner portion of the first crystal side which is interior to the inner perimeter of the first electrode. In one preferred embodiment, the first electrode is shaped at least in part as a circular or oval ring, which defines an outer portion of the first crystal side exterior to the ring, and an inner portion of the first crystal side which is interior to the ring. In this manner, a greater surface area of active crystal sites remain available for adsorption, for example, of species-specific complementary material (e.g. an antibody) in contrast to conventional quartz crystal-solid electrode arrangements, in which only the active crystal sites exterior to the outer perimeter of the solid electrode are available for adsorption. An example of such a conventional quartz crystal-solid electrode arrangement is depicted in U.S. Pat. No. 4,242,096 (Oliveira et al.). In other embodiments of this invention, the first electrode may have a triangular, square or other ring shape, as long as active crystal sites both interior and exterior to the electrode remain available for adsorption.

A second electrode is integral to the second crystal side. The second electrode may be of any design provided it is capable, in cooperation with the first electrode, of providing a measurement signal based upon the resonant frequency of the detector oscillator. In one preferred embodiment, the second electrode is disk-shaped, as depicted, for example, in U.S. Pat. No. 4,242,096 (Oliveira et al.).

The first and second electrodes may be made from gold, silver, nickel, chromium or tantalum, respectively. In a preferred embodiment, the first electrode is gold and the second electrode is gold. In a particularly preferred embodiment, the first electrode is a gold circular ring-shaped electrode and the second electrode is a gold solid circular-shaped electrode. The first and second electrodes may be integrated into the first and second crystal sides, respectively by any conventional means. In a preferred embodiment, this is accomplished via vacuum depositing the desired metal electrode material on the respective crystal side.

The crystal detector oscillator may be supported by means operatively coupled to the crystal detector oscillator for conveying the measurement signal obtained from the crystal detector oscillator for signal processing. In one preferred embodiment, the crystal oscillator detector is supported by a pin and base plug arrangement as described, for example, in U.S. Pat. No. 4,242,096 (Oliveira et al.). Other conventional means such as connection leads, clips, etc. may also be employed to convey the measurement signal for signal processing.

Figure 2B:
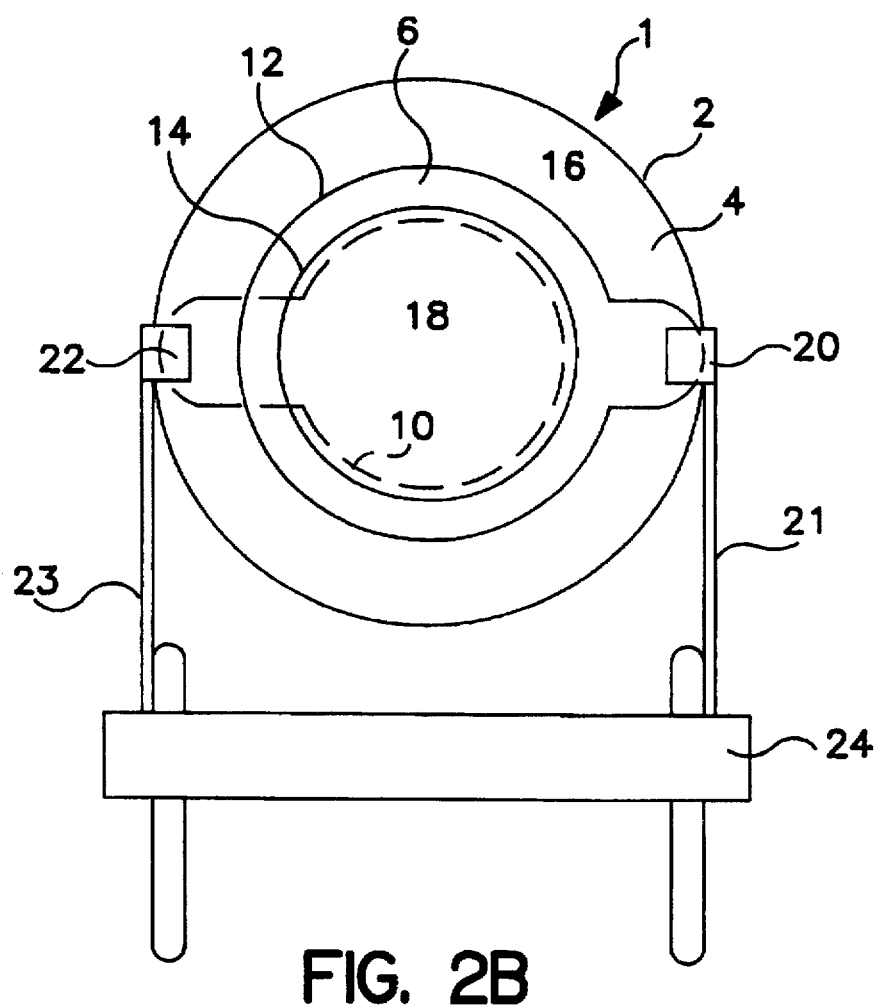
FIG. 2B depicts a top view of a preferred embodiment of the chemical sensor of this invention.

FIG. 2A depicts a side view of a preferred embodiment of the chemical sensor 1. In FIG. 2A crystal detector oscillator 2 is an AT-cut quartz crystal having first crystal side 4 having first electrode 6 integral thereto and second crystal side 8 having second electrode 10 integral thereto. FIG. 2B depicts a front view of the first crystal side 4 of the sensor 1 of FIG. 2A. In FIG. 2B, first electrode 6 is a gold, partially circular ring shaped electrode which has been vacuum deposited as a thin film and is integral to first crystal side 4. The ring-shaped portion of first electrode 6 has an outer perimeter 12 and an inner perimeter 14, thereby defining outer portion 16 of the first crystal side and inner portion 18 of the first crystal side. In this manner, active crystal adsorption sites located at outer portion 16 and inner portion 18 remain available for adsorption, and are not covered by first electrode 6. Second crystal side 8 (not shown in FIG. 2B) has a disk-shaped gold second electrode 10 (shown with dashed lines in FIG. 2B) which is integral to second crystal side 8 and has been vacuum deposited as a thin film on second crystal side 8. Also depicted in FIG. 2B are a preferred embodiment of means operatively coupled to the crystal detector oscillator 2 for conveying the measurement signal obtained by crystal detector oscillator 2 for signal processing (not shown in FIG. 1B); namely pins 20 and 22 which are operatively coupled to first and second electrodes 6 and 10, respectively, and which in turn are operatively coupled by leads 21 and 23 to base plug 24. Base plug 24 may in turn be operatively coupled to signal processing means (not shown).

An example of a crystal detector oscillator of the present invention is a Model QC-10-R Laboratory Quartz Crystal available from Elchema (Potsdam, N.Y.). This is an AT-cut quartz crystal having a first crystal side with a gold ring-shaped electrode integral thereto. The ring-shaped electrode's outer perimeter has a radius of 3.5 mm, and the area of the ring-shaped electrode is 0.1885 cm$^2$. The first crystal side has an exposed quartz crystal area of 0.1963 cm$^2$. The second crystal side has a solid gold disk-shaped electrode integral thereto. The disk-shaped electrode has a radius of 2.5 mm. The Model QC-10-R operates in the shear mode with a 10 Mhz frequency.

In a preferred embodiment, the chemical sensor is fixed or attached to container means for holding a solution sample. Thus, for example, in a particularly preferred embodiment the sensor may be removably or permanently mounted in a container such as a glass beaker by cutting an opening in the side wall of the container and attaching the sensor via epoxy or other conventional means. In another particularly preferred embodiment, the sensor is removably vertically mounted via epoxy in a cut-out opening in a 25 ml glass beaker. In this manner, the detector may be contacted with a solution containing the species-specific complementary material and a solution containing the predetermined chemical species. Also, the detector is removable for easy cleaning, repair, etc. The sensor is used to detect the concentration of a predetermined chemical species in solution. As used in this specification and the appended claims, the term "predetermined chemical species" refers to any chemical species which is identified and chosen as the subject matter of interest prior to use of the invention. Examples of such species include any antigen which has a corresponding antibody. Particularly preferred antigens are thyroxine and calcitonin.

A species-specific material which is complementary to the species may be adsorbed onto the active crystal sites of the first crystal side (i.e. the active sites of exposed crystal surface residing in the exterior and interior portions of the first crystal side), and the first crystal side may thereafter be contacted with the species-containing solution, thereby causing adsorption of molecules of the predetermined species onto the complementary material-adsorbed active crystal sites. The difference in the measured resonant frequencies of the complementary material-adsorbed sensor and the complementary material plus species adsorbed sensor is indicative of and may be correlated with the concentration of the predetermined species in solution. As used in this specification and the appended claims, the term "complementary material" refers to a material or substance which is capable of interacting with a given predetermined chemical species so as to cause adsorption or binding of the chemical species to the complementary material. Examples of such complementary materials include antibodies which are capable of interacting with predetermined antigens, such as anti-thyroxine (i.e. an antibody) to interact with thyroxine (i.e. an antigen) and anti-calcitonin (i.e. an antibody) to interact with calcitonin (i.e. an antigen).

In a preferred embodiment, this invention is useful for the analysis of predetermined chemical species in solution for both humans and animals. In addition, all hormones, enzymes, and antigens in solution may be analyzed using this invention. More specifically, this includes invaders to the immune and hormonal systems such as viruses, including HIV, allergens, species which cause allergic or immunological reactions, species which cause or are related to the coagulation of blood, species which are related to or cause or enhance chemical or biochemical reactions and polymerization reactions. This invention may also be useful in the analysis of chemical reaction kinetics, as well as for other chemical applications such as analysis of the degradation of coatings applied to the sensor first crystal side such as latex coatings, metallic coatings, paints, lacquers, polymer coatings such as polyurethanes, varnishes, plastics, rubbers, cements, aggregates, asphalts, amalgams, bonding materials, epoxies, adhesives, resins and the like, the analysis of polyaromatic hydrocarbons (PAH), chlorinated hydrocarbons, and other chemical species.

Hormones which may be analyzed using this invention include: steroid hormones such as estrogens, androgens, progesterone, testosterone, estradiol; adrenal cortical hormones such as cortisone; cardiac glycosides and bile acids. Additional hormones may include cortisol, glucagon, epinephrine, catecholamine hormones, peptide hormones, protein hormones, thyroid hormones (i.e. $T_4$, TSH, etc.), insulin, growth hormone, and human placental lactogen.

Enzymes which may be analyzed using this invention include: APS reductase, alanine transaminase, Tyrosine transaminase, Tryptophan pyrrolase, Serine dehydrase, Pyruvate Carboxylase, Phosphoenolpyruvate carboxykinase, phosphoglyceraldehyde dehydrogenase, Aldolase, Fructose 1,6-diphosphatase, Phosphohexoisomerase, Glycogen synthetase, Glucose 6-phosphatase, Arginine synthetase, Arginosuccinase, Arginase, Succinic dehydrogenase, adenylate cyclase, protein kinase, Adenosine Triphosphatase, Lactase, Glycerol ester hydrolase, cholestrol ester hydrolase, Phospholipidase $A_2$, Colipase, Polymerase, Phosphodiesterase, and Adenylate cyclase.

Antigens which may be analyzed using this invention include the antigens for such illnesses as: Lyme disease, HIV, Syphillis, gonorrhea, mumps, chicken pox, measles, Eppstein-Barr, diseases for which there is secretion of immunoglobulins that are specific to the causative antigen, meningitis, rickettsia, Rocky Mountain Spotted Fever, atypical mycobacterial infections, cholera, coccal infections, conjunctivitis, E. coli infections, mycobacterial infections, Salmonella infections, Shigella infections, mycoplasma infections, Urinary tract infections, tetanus, hepatitis, bacteremia, endocarditis, pneumonia, osteomyelitis, cellulitis, pharyngitis, otitis media, Scarlet fever, Erysipelas, Septicemia, brain and other abcesses, Arthritis, laryngotracheitis, enterobacter aerogenes infections, plague, serratia infections, Brucellosis, Legionnaires disease, Leprosy, tuberculosis, Typhus fever, Q fever, Murine typhus, Brill's disease and Chlamydia.

In a preferred embodiment, the method of using the sensor for detecting the concentration of predetermined chemical species in solution comprises:

(a) providing the chemical sensor of this invention;

(b) contacting the first crystal side of the sensor with a solution containing a predetermined species-specific complementary material to the predetermined chemical species;

(c) measuring the resonant frequency of the crystal detector oscillator after contacting with the solution containing the complementary material;

(d) contacting the first crystal side with a solution containing the predetermined chemical species;

(e) measuring the resonant frequency of the crystal detector oscillator after contacting the first crystal side with the species-containing solution; and (f) comparing the difference in resonant frequencies measured in steps (c) and (e) to determine the concentration of the species in the species-containing solution.

To eliminate various sources of error relating to measurement of the resonant frequencies, in a preferred embodiment the method additionally comprises the steps of providing a reference oscillator having a reference resonant frequency, comparing the difference between the resonant frequency measured in step (c) and the reference resonant frequency to obtain a first normalized resonant frequency, comparing the difference between the resonant frequency measured in step (e) and the reference resonant frequency to obtain a second normalized resonant frequency, and comparing the difference between the first and second normalized resonant frequencies to determine the concentration of the chemical species in the species-containing solution.

The sensor and method of its use are advantageous in that the sensor is easily cleanable after its use, and thus is adaptable to a variety of clinical settings where, for example, the blood samples of multiple patients are analyzed using the invention. Thus, after a given patient's blood sample is analyzed for a predetermined species, and the difference in resonant frequencies is measured as in step (f) set forth above, the first crystal side of the sensor may be contacted with a cleaning solution to remove the adsorbed chemical species and complementary material from the surface of the first crystal side and regenerate active sites on the surface of the first crystal side for subsequent adsorption by fresh complementary, material and chemical species from the next patient's blood sample.

The apparatus of this invention comprises the chemical sensor of this invention and sensor detecting means operatively coupled to the sensor for detecting the resonant frequency of the crystal detector oscillator and providing a detector output signal representative of the crystal detector oscillator resonant frequency.

The sensor detecting means may be or include any means capable of detecting a frequency signal, such as an oscilloscope, etc. The apparatus may additionally comprise, in a preferred embodiment, display means operatively coupled to the sensor detecting means for displaying the detector output signal, and signal processing means such as computer software or firmware capable of suitably filtering out random variations in the raw data received (i.e. the signal received from the sensor). Display means, as hereinabove described, may be operatively coupled by any well known, conventional means to the signal comparison means for displaying the difference output signal. The display means may be, for example, an oscilloscope screen, a computer monitor in conjunction with conventional signal processing equipment, a suitable suite of system software or firmware, etc.

In another preferred embodiment, the apparatus may additionally comprise a reference oscillator, reference detecting means operatively coupled to the reference oscillator for detecting the resonant frequency of the reference oscillator and providing a reference output signal representative of the reference oscillator resonant frequency, and signal comparison means operatively coupled to the sensor detecting means and the reference detecting means for comparing the difference between the detector output signal and the reference output signal and providing a difference output signal.

Figure 3:
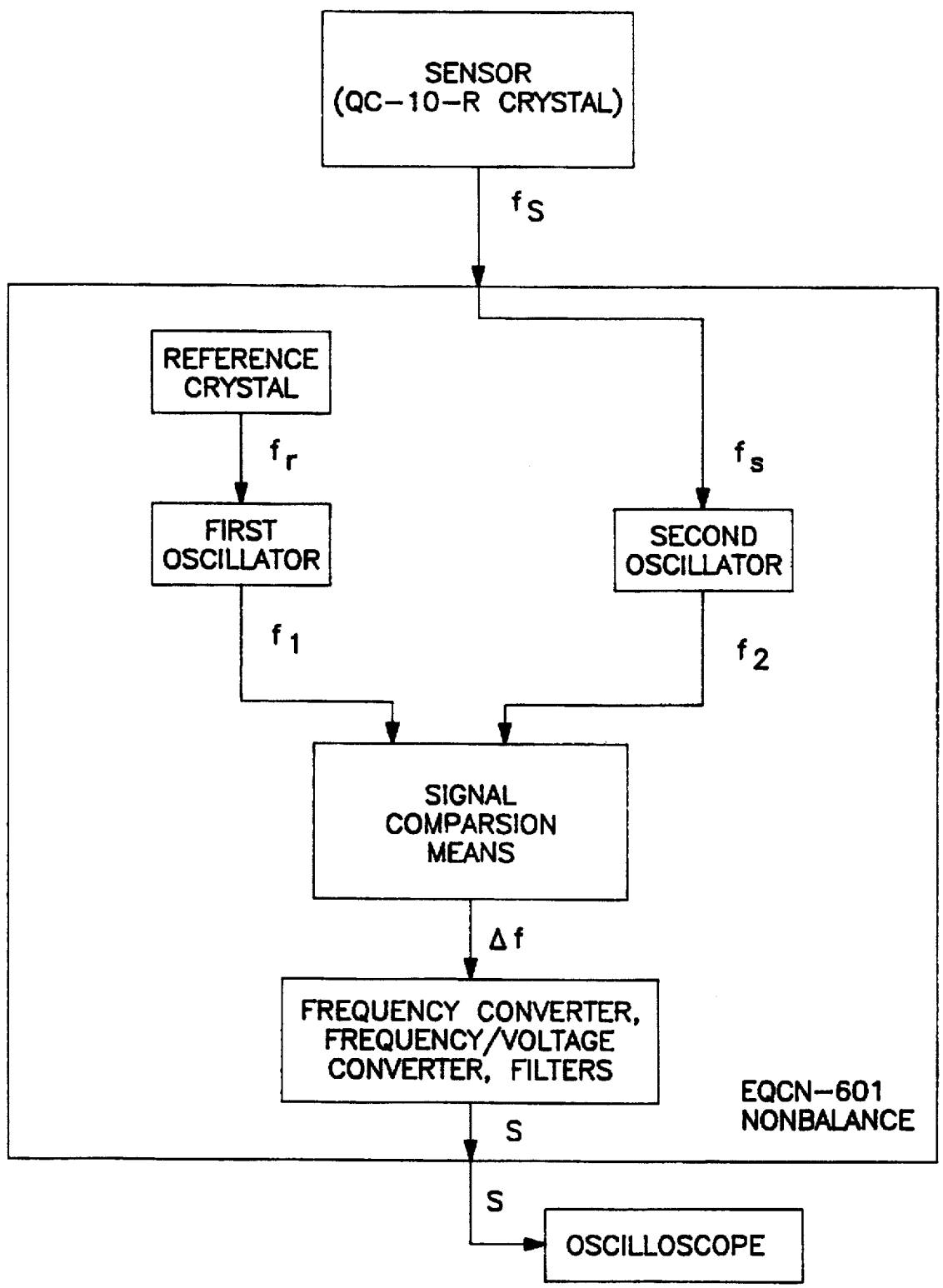
FIG. 3 is a block diagram of one embodiment of the apparatus of this invention.

In a particularly preferred embodiment of the apparatus, as depicted in block diagram form in FIG. 3, the sensor employed is an Elchema Model QC-10-R Laboratory Quartz Crystal operatively coupled by well known, conventional means to sensor detecting means which are a Model EQCN-600 Electrochemical Quartz Crystal Nanobalance system manufactured by Elchema. The EQCN-600 system is employed to obtain the resonant frequency of the sensor, and comprises a Model EQCN-601 nanobalance, Model EQCN-602 "Faraday Cage," and Model EQCN-603 "Remote Probe Unit," all manufactured by Elchema. The Model EQCN-601 nanobalance exemplifies one embodiment of sensor detecting means which may be employed in this invention. The Model QC-10-R detector is operatively coupled via model EQCN-603 Remote Probe Unit to the Model EQCN-601 nanobalance. The detector and remote probe unit are contained within the Model EQCN-602 Faraday Cage, which acts to isolate the detector from various sources of error (e.g. power fluctuations, electromagnetic variations, etc.). The Model EQCN-601 nanobalance comprises a first oscillator which is operatively coupled to and driven by a reference oscillating crystal, thereby providing a reference oscillator resonant frequency $f_r$ and a reference output signal $f_1$ representative of the reference oscillator resonant frequency. The resonant frequency of the sensor upon adsorption of the complementary material or complementary material plus chemical species is represented as $f_s$. The sensor is operatively coupled to and drives a second oscillator, thereby providing a signal $f_2$ representative of the resonant frequency of the detector. Signal comparison means operatively coupled to the first and second oscillators compares signals $f_1$ and $f_2$ and provides a difference output signal $\Delta f$, which in turn is processed by conventional means using a frequency counter or meter, frequency/voltage converter and various filters and amplifiers which comprise the Model EQCN-601 to yield a detector output signal S representative of the normalized crystal detector oscillator resonant frequency. The Model EQCN-601 is in turn operatively coupled to an oscilloscope for quantitative measurement of the detector output signal.

Figure 4:
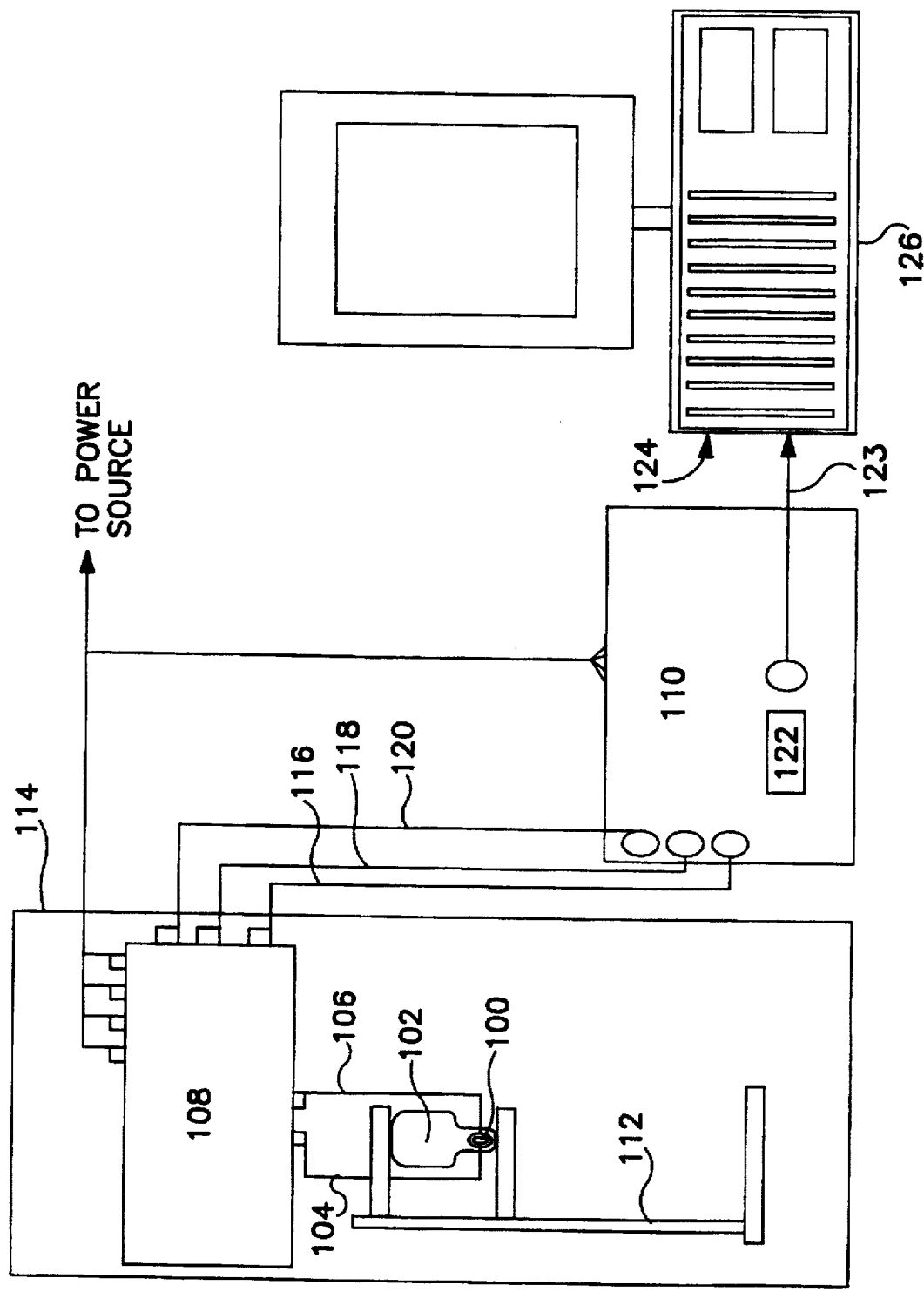
FIG. 4 is an illustration of another embodiment of the apparatus of this invention.
Figure 17:
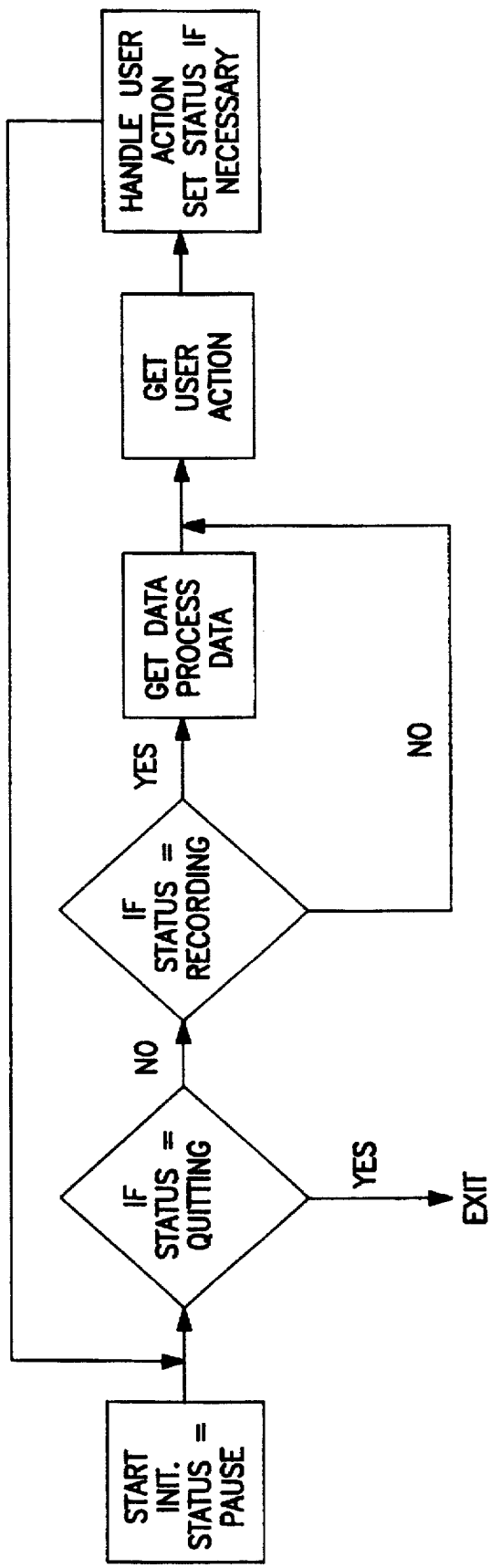
FIG. 17 depicts a block diagram schematic representation of a data processing scheme used in a preferred embodiment of the invention.

In another preferred embodiment the sensor detecting means, (for example, Elchema Model EQCN-601 nanobalance) may be operatively coupled to interface means for converting the data output signal into a displayable form, and display means may be operatively coupled to the interface means to display the data output signal. A particularly preferred embodiment is depicted in FIG. 4. In FIG. 4, chemical sensor 100 (e.g. Elchema Model QC-10-R Laboratory Quartz Crystal) is vertically mounted in a side wall of a 25 ml glass beaker 102. First and second electrodes of the sensor (not shown) are connected via leads 104 and 106 to sensor detecting means 108 (e.g. Elchema Model EQCN-603 Remote Probe Unit) and 110 (e.g. Elchema Model EQCN-601 nanobalance). The stand 112 supporting beaker 102, beaker 102 comprising sensor 100, and sensor detecting means 108 are all contained within means for shielding the sensor from disturbances (e.g. Elchema Model EQCN-602 Faraday Cage) 114. Sensor detecting means 108 is operatively coupled via leads 116, 118, 120 to sensor detecting means 110, which has an LCD frequency display 122 for displaying the normalized sensor frequency. Sensor detecting means 110 is in turn operatively coupled via lead 123 to interface means 124, which in a preferred embodiment is a National Instruments data acquisition board (i.e. LAB-PCt with its attendant "NI-DAQ" software interactively employed with Lab Windows User Interface) and a custom set of software routines in the "C" programming language to acquire the data received, and display it in a graphically pleasing and useable manner. The custom software accurately determines time intervals, keeps track of system status and calibration, filters out spurious signals, and oversees all phases of the automatic acquisition of data. The software also evaluates the relationship of change in mass to change in frequency, finds average frequency, updates status, repeats the process, and stores tables of results. A general schematic of the software is set forth in FIG. 17. A complete program listing of the software employed in a preferred embodiment of the invention is set forth in FIG. 18. The interface means 124 is operatively coupled to display means 126 (e.g. a personal computer with monitor). In a preferred embodiment, the LAB-PCt is operatively coupled to a Dell 486 D66 computer with a Dell UltraScan Monitor. However, any suitable personal computer (PC) may be used, and any suitable data acquisition board and attendant driver software may be used. For example, such boards include a Metrabyte board, and Analogic board, as well as the already-discussed National Instruments board, which was chosen for use due to its programming ease. The custom "C" software program may readily be made independent of the Lab Windows package. The Lab Windows software was used due to its screen display qualities.

The specifications for the Elchema EQCN-600 system are as set forth in Table 1:

TABLE 1

| Measurement Ranges | |
|---|---|
| Frequency Difference Resolution | 0–500 kHz, 0–5 MHz |
| Frequency Difference (5 MHz range) Operating Parameters | .1 Hz (500 kHz range), 10 Hz |
| Reference Crystal Frequency | .10.000 MHz |
| Power Supply | .110 V or 220 V, 50–60 Hz |
| Dimensions: | |
| Instrument | .4.5 H × 17 W × 16.5 D, inch |
| Faraday Cage | .24 H × 16 W × 9 D, inch |

In a preferred embodiment, the method of using the apparatus of this invention comprises: (a) providing the chemical sensor of this invention and sensor detecting means operatively coupled to the sensor for detecting the resonant frequency of the crystal detector oscillator and providing a detector output signal representative of the crystal detector oscillator resonant frequency;

(b) contacting the first crystal side of the sensor with a solution containing a predetermined species-specific complementary material to the predetermined chemical species;

(c) measuring the resonant frequency of the crystal detector oscillator after contacting with the solution containing the complementary material;

(d) contacting the first crystal side with a solution containing the predetermined chemical species;

(e) measuring the resonant frequency of the crystal detector oscillator after contacting the first crystal side with the species-containing solution; and (f) comparing the difference in resonant frequencies measured in steps (c) and (e) to determine the concentration of the species in the species-containing solution.

In another preferred embodiment, the measurements made in steps (c), (e) and (f) may additionally comprise the use of the above-described software processing.

In another preferred embodiment, the method may additionally comprise providing a reference oscillator, providing reference detecting means operatively coupled to the reference oscillator for detecting the resonant frequency of the reference oscillator and providing a reference output signal representative of the reference oscillator resonant frequency, and signal comparison means operatively coupled to the sensor detecting means and the reference detecting means for comparing the difference between the detector output signal and the reference output signal and providing a difference output signal. The difference between the resonant frequency measured in step (c) above and the reference resonant frequency is determined to obtain a first normalized resonant frequency. The difference between the resonant frequency measured in step (e) and the reference resonant frequency is also determined to obtain a second normalized resonant frequency. The difference between the first and second normalized resonant frequencies is obtained to determine the concentration of the chemical species in the species-containing solution.

In another preferred embodiment, the resonant frequency of the reference oscillator and crystal oscillator, the difference output signal and the comparison of the normalized frequencies may be accomplished in conjunction with the above-described software processing and suitable error reduction algorithms and software processing. The concentration of the species in solution may also be determined using the above-described software processing.

In another preferred embodiment, the sensor and apparatus of this invention may be used to measure a change in the sensor mass relating to the interaction of the first crystal side of the sensor with a solution. For example, the first crystal side may be coated and the coated sensor mass change due to degradation of the coating may be measured.

In a particularly preferred embodiment, this invention may be used to determine concentrations of thyroxine (also known as $T_4$) in human blood. Thyroxine is a thyroid hormone, and is a chemical messenger that is released directly into the bloodstream and circulates throughout the body but only affects certain target organs. The more thyroxine there is in the bloodstream, the greater the rate at which chemical reactions occur, also known as the body's metabolic rate and physical development.

The study of the thyroid gland and the role of thyroxine in the body arose from observations made, first in ancient times and, later during sixteenth century Europe, that thyroid gland enlargements, also called goiters, were medical disorders and could be described as specific syndromes. The occurrences of goiter in severely hypothyroid children (cretins) led to the conclusions that developmental abnormalities were related to low levels of thyroxine in the system and that thyroxine was instrumental to normal growth and development.

Today, thyroxine levels are monitored for a variety of patients using a variety of diagnostic tests. Patients who are pregnant, or taking oral contraception, or undergoing estrogen therapy, for example, all need to have their thyroxine levels checked regularly. The diagnostic techniques used to determine thyroxine levels in blood include RIA and Enzyme-linked immunoassay (ELISA). RIA is a competitive assay, that is the nonradioactive thyroxine competes with a constant amount of $^{125}I$-$T_4$, where $^{125}I$ is radioactive iodine that is substituted for the iodine attached to a thyroxine molecule, for binding sites on a limited amount of $T_4$ antibody receptors coupled to some solid phase, such as beads. The $^{125}I$ labeled antigen is present in fixed quantities, as is the antibody, and the unlabelled antigen (e.g. test sample) is present in unknown amounts. The mixture is allowed to equilibrate and the antibody-bound antigen is separated from the unbound antigen. The more labeled hormone combined with antibody, the lower the hormone level in the test sample. The amount of isotope labeled hormone complexing with the hormone antibody varies inversely with the quantity of unlabelled hormone in the test sample.

ELISA is another labeling method for detecting hormonal concentration, except in this case the label is an enzyme. An enzyme labeled molecule, either an antigen or antibody, is attached to some insoluble support, such as plastic beads or plastic agglutination plates. To a mixture of this is added the test material, the antigen or antibody which is being measured. The test material competes with the added labeled antigen or antibody for the material attached to the plastic plates. The enzyme substrated material is subjected to colorimetry and the concentration of the test material can be determined.

The immune system is a recognition system that distinguishes "self" (the body's own molecules) from "nonself" (foreign molecules). When the immune system detects a foreign substance, called an antigen, it responds with a proliferation of cells that either attack the invader directly or produce specific defensive proteins called antibodies, which help counter the antigen in various ways. The word antigen is actually a contraction of "antibody generating," a reference to the foreign agent's ability to provoke the immune system to react. It is this antigen-antibody interaction that allows for the regulation of thyroxine levels in the body.

The IUPAC name for $T_4$ is 3,5,3',5'-tetraiodothyronine and its common name is thyroxine. Thyroxine has two possible rotary forms, the levo (L) form and the dextro (D) form. It occurs naturally in the L form. In a preferred embodiment, this invention is directed to the L-$T_4$ to Anti-$T_4$ interaction. The L-$T_4$ is the antigen and the Anti-$T_4$ is the serum antibody. Thyroxine is an iodinated amino acid and a relatively small molecule. In immuno-response, it is not the entire cell or invading organism that is identified as foreign, but biochemical markers that cover the invader. In general, antibodies identify localized regions on the surface of an antigen, called antigenic determinants.

Antibodies constitute a class of proteins called immunoglobulins, Ig. An immunoglobulin has the capability of recognizing and binding to an antigen molecule as well as an effector mechanism to assist in the destruction and elimination of that antigen. Typical antibody molecules consist of two pairs of polypeptide chains—two short identical light (L) chains and two longer identical heavy (H) chains. The chains are joined by disulfide bridges and noncovalent associations to form a Y-shaped molecule. The two arms of the Y, where the light and heavy chains terminate form the area called the antigen-binding site.

Figure 5:
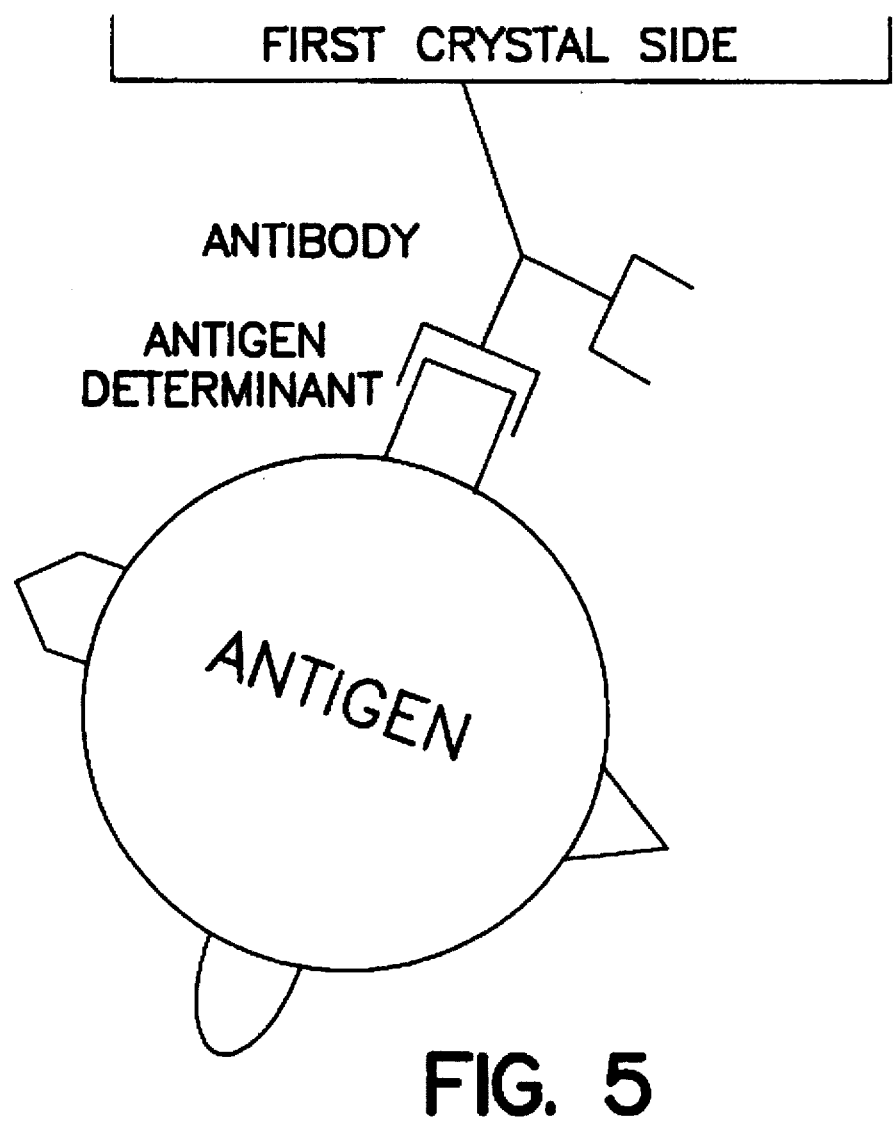
FIG. 5 is an illustration of an antigen-antibody-active crystal site complex.

There are no covalent bonds involved in the interaction between an antibody (antigen-binding site) and an antigen (antigenic determinants). Because of this, the binding forces that comprise the antigen-antibody interactions are somewhat weak. These binding forces mainly consist of van der Waals forces, electrostatic forces, and hydrophobic forces, all of which require a very close proximity between the interacting moieties. Thus the interaction requires a very close fit between an antigen's antigenic determinant and the antibody's antigen-binding site. As illustrated in FIG. 5, in the present invention an antibody (e.g. anti-thyroxyine) is adsorbed to an active site on the sensor's first crystal side, and the antigen molecule (e.g. thyroxine) is adsorbed to the antibody.

As a result of the low levels of energy involved in the antigen-antibody interaction, the antigen-antibody complexes can be readily dissociated by low or high pH or by high salt concentrations. Accordingly, the sensor of this invention may be cleaned for reuse by employing such means.

The following examples illustrate various preferred embodiments of this invention. It will be understood that the following examples are merely illustrative and not meant to limit the invention in any way. All experiments were performed using the Elchema Model QC-10-R Laboratory Quartz Crystal operatively coupled to the Elchema Model EQCN-600 nanobalance system as previously described. Data obtained were recorded manually, at a frequency of one data point per minute.

EXAMPLE 1

The biochemicals that were used include: Sigma (St. Louis, Mo.) immunochemical grade L-thyroxine antiserum (Anti-$T_4$) developed in rabbit immunogen (this product was provided as undiluted antiserum containing 0.1% sodium azide as a preservative), Sigma research grade L-thyroxine free acid ($T_4$), CAS#51-48-9, Sigma diagnostic grade Phosphate Buffered Saline (PBS) dry powder blend, CAS#1000-3, Aldrich (Milwaukee, Wi.) laboratory grade sodium hydroxide (NaOH) pellets (97+% pure) CAS#22,146-5, and Fisher (Pittsburgh, Pa.), and laboratory grade concentrated hydrochloric acid (HCl), CAS#7647-01-0. Phosphate buffered saline was used to keep the protein solutions at a working pH of 7.4. The buffer consisted of sodium chloride (0.12M), potassium chloride (0.0027M), and phosphate salts (0.01M).

The essential chemicals utilized in the experimentation and their purpose were as follows:

| REAGENTS | PURPOSE USED |
| --- | --- |
| Anti-$T_4$ | Used as the quartz crystal sensor coating |
| $T_4$ | Used for the standard addition of antigen to the blood serum |
| PBS | Buffering reagent for the Anti-$T_4$ |
| NaOH | Diluent for the $T_4$ free acid |
| HCl | Cleaning solution for the quartz crystal sensor |

A series of Anti-$T_4$ solutions were prepared. The entire contents of one packet of phosphate buffered saline powder were dissolved with deionized water into a 1000 mL volumetric flask, making 0.01M PBS. The Anti-$T_4$ was diluted into a series of working dilutions in the 0.01M phosphate buffered saline. These working dilutions had concentrations of: 1:10, 1:100, 1:1000, 1:10,000, 1: 100,000, 1:1,000,000, 1: 10,000,000 mL Anti-$T_4$ in 0.01M PBS and were stored at 4 °C. The undiluted antiserum was stored at −20° C.

A series of $T_4$ solutions was also made. Sodium hydroxide, 0.05M, was prepared into a 500 mL volumetric flask. A stock standard solution of 1.0 g/L $T_4$ free acid was made in the 0.05M sodium hydroxide. From this stock solution, a series of $T_4$ working dilutions were made up. They had concentrations of 1:10, 1:100, 1:1000, 1:10,000, 1:100,000 g $T_4$ per liter solution diluted in 0.05M sodium hydroxide.

The efficacy with a blood serum matrix was tested by the use of Sigma research grade rat serum—aseptically filled. The rat serum was used as received.

EXAMPLE 2

Calibration Curves

Calibration experiments were performed to obtain calibration curves for the thyroxine solutions prepared in Example 1.

The general outline of the method employed was as follows:

1. Cleaning of the quartz crystal and beaker.
2. Addition of the sensor coating (Anti-$T_4$).
3. Removal of Anti-$T_4$ solution 10 minutes after start of trial run.
4. Addition of sample containing antigen ($T_4$).

The calibration curves used to determine the optimum Anti-$T_4$ coating concentration were made by performing trial runs with a fixed thyroxine concentration and varying Anti-$T_4$ concentrations. The calibration curves used to determine whether or not the frequency varied linearly with changes in concentration of thyroxine were obtained by performing trial runs with a fixed Anti-$T_4$ concentration and varying concentrations of the L-thyroxine.

The specific outline of protocol for generating the sensor coating calibration curves and the confirmation of linearity of varying L-thyroxine was as follows:

1. 5 mL of 1:1000 Anti-$T_4$ in 0.01M PBS was added to an electrochemical cell that was newly cleaned.

In determining the sensor coating calibration curves, varying concentrations of Anti-$T_4$ were tested with a fixed amount of $T_4$ (1.0 g/L in 0.05M NaOH). These concentrations included: 1:100, 1:1,000, 1:10,000, 1:100,000, 1:1,000,000, 1:10,000,000 mL Anti-$T_4$ in 0.01M PBS.

2. 10 minutes after the addition of the sensor coating, the remaining solution was poured out and 5 mL of $T_4$ in 0.05M NaOH were added to the cell. The concentrations of $T_4$ added varied from 1:1 $T_4$ to 1:100,000 $T_4$ in 0.05M NaOH.
3. The frequency changes were monitored and recorded at intervals of one minute.
4. 5 minutes after the addition of the $T_4$, the contents of the beaker were allowed to flow to waste.
5. The electrochemical cell and sensor were cleaned and readied for the subsequent trial.

EXAMPLE 3

Standard addition curves for additions of thyroxine to rat serum were generated as follows:

The procedures used for generating standard addition curves to rat serum were as follows:

1. 5 mL of 1:1000 Anti-$T_4$ in 0.01M PBS were added to the cell.
2. 10 minutes later, the remaining Anti-$T_4$ solution was poured out and 5 mL of the undiluted rat serum was added to the cell.
3. 5 minutes after that, and for every 5 minute interval lasting for approximately 40 minutes, 0.25 mL of varying concentrations of L-$T_4$ in 0.05M NaOH were added.
4. The cell and sensor were cleaned and readied for subsequent trials.

The cleaning procedures were as follows:

1. Samples were drained from the electrochemical cells.
2. 5 mL of 0.05M HCl were added to the cell and allowed to sit for approximately 3 minutes and then drained.
3. 10 mL of de-ionized water were added to the cell and then drained.

Haschemeyer and Haschemeyer have investigated the dynamics of protein conformation and methods for denaturing the Anti-$T_4$ immunoglobulin were obtained from their work. The presence of hydrochloric acid in the immunoglobulin solution causes the polypeptide chains to unfold and, therefore to precipitate into the acidic medium, which is then poured out.

EXAMPLE 4

Frequency Difference Stability Study

Experiments were conducted to determine the time period necessary to obtain accurate results for frequency difference. The results are depicted in FIG. 6.

Figure 6:
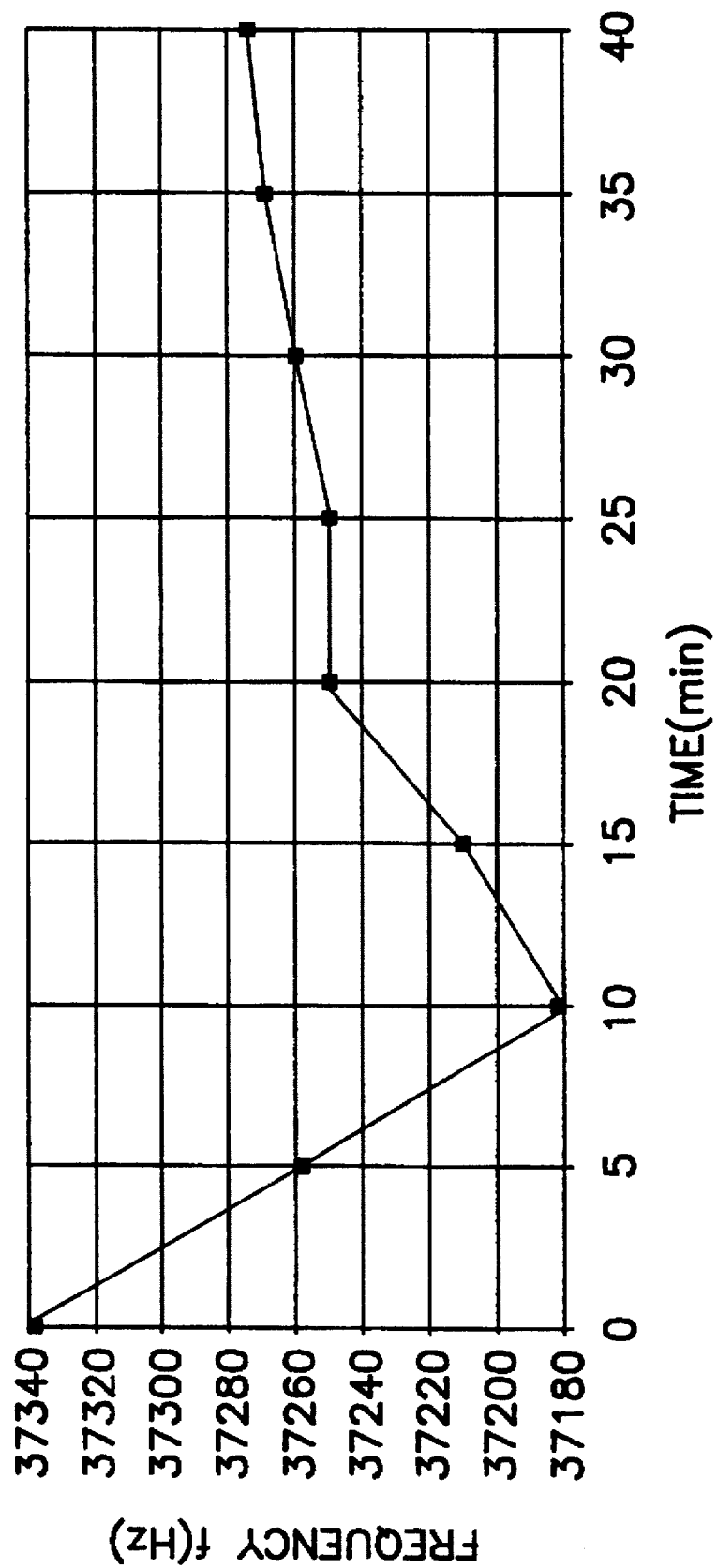
FIG. 6 depicts a plot of frequency vs. time for the sensor after addition of thyroxine.

As can be seen from FIG. 6, the most significant change in frequency difference occurred at a time of ten minutes after the addition of thyroxine to the sensor. Thus, it was concluded that trial times lasting approximately twenty minutes in total were sufficient in order to obtain the necessary results.

EXAMPLE 5

Optimum Anti-$T_4$

Sensor Coating Concentration Study

The optimum amount of Anti-$T_4$ necessary to give a monolayer of coating that encompassed the total active area of the quartz crystal was determined. Table 2 lists the changes in frequency observed at different coating dilutions of the Anti-$T_4$ in the PBS buffer.

TABLE 2

Sensor Coating Optimization Data

| Coating Dilution (mL AT$_4$:mL Sol'n) | Frequency (Hz) |
|---|---|
| 1:100 | 230 |
| 1:1000 | 257 |
| 1:10,000 | 201 |
| 1:100,000 | 173 |
| 1:1,000,000 | 113 |
| 1:10,000,000 | 12 |

According to the table, the changes in frequency difference were greatest at Anti-$T_4$ dilutions ranging from 1:10,000 to 1:10,000,000. The frequency differences levelled off somewhat near 1:1000, and changed again at 1:100. In addition to the tabulated coating amounts, a dilution of 1:10 was tried, but the frequency difference readings fluctuated greatly. Apparently at Anti-$T_4$ working dilutions of less than 1:100, stearic hindrances from the big and bulky immunoglobulins occur and disrupt the binding characteristics.

Also, at low dilutions (i.e. high concentrations) of Anti-$T_4$, a phenomenon known as the "dose-hook" effect occurs. In this instance, the binding sites that attach $T_4$ molecules to the antiserum become swarmed and the interactions break down, and it appears that no interactions occur. One would expect that, at higher concentrations of antibody more binding should occur, however the results are just the opposite. In fact, it has been observed that at both high and low concentrations of antibody, the same outcome is realized, i.e. low binding readings.

Figure 7:
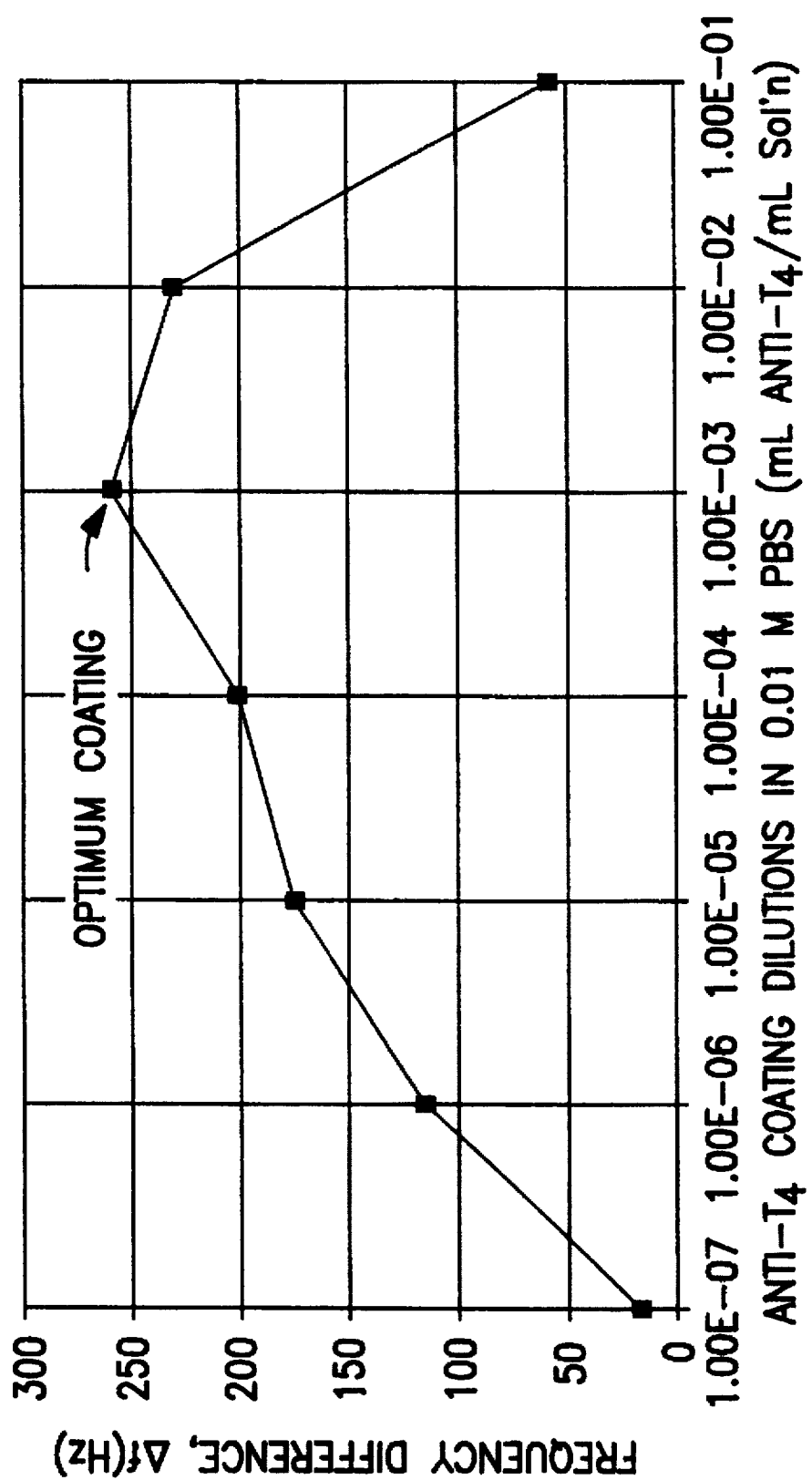
FIG. 7 depicts a plot of frequency difference vs. anti-thyroxine coating dilutions of anti-thyroxine in PBS.
Figure 8:
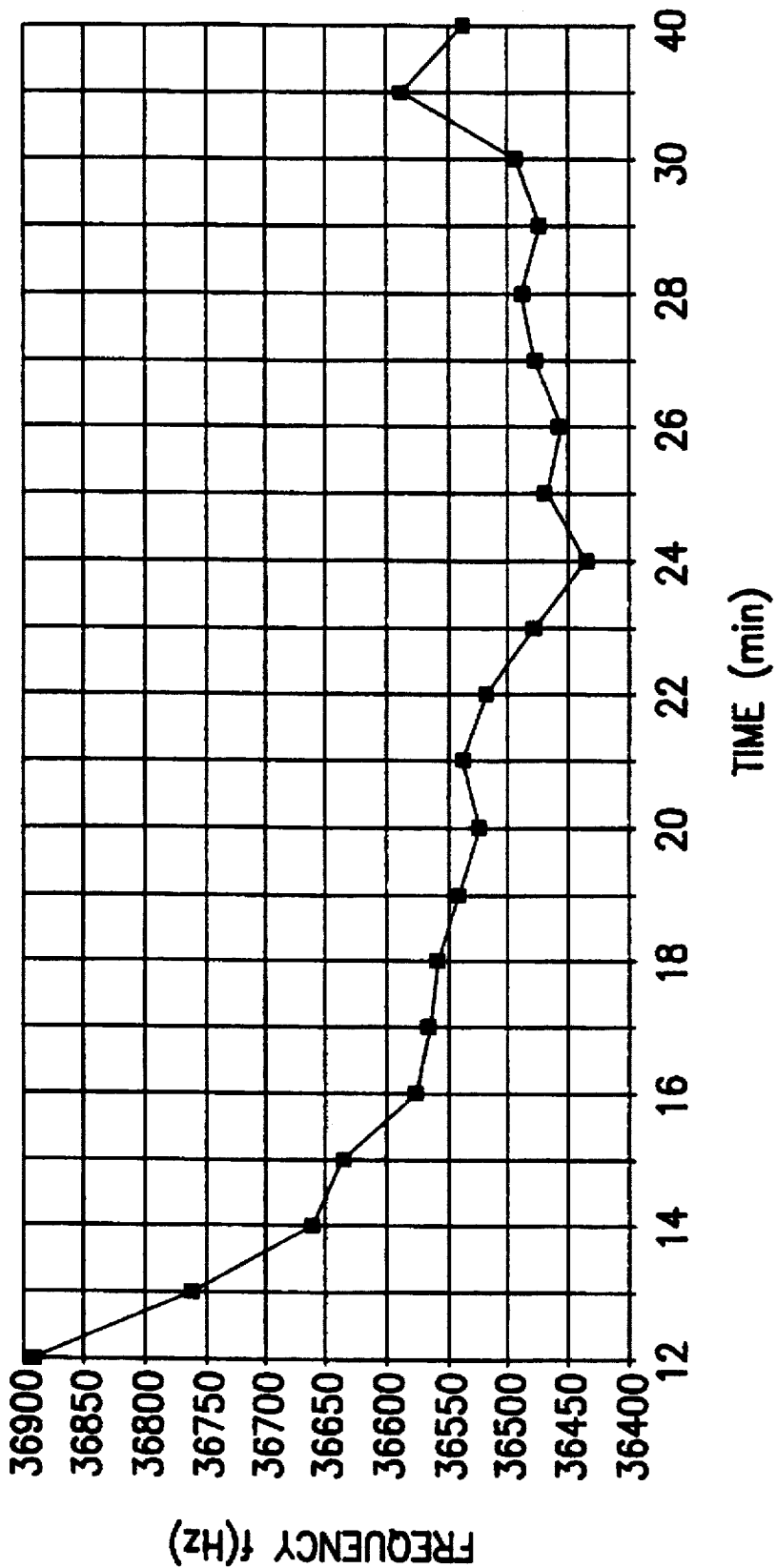
FIG. 8 depicts a plot of frequency vs. time for a 1:1000 dilution of anti-thyroxine in PBS.
Figure 9:
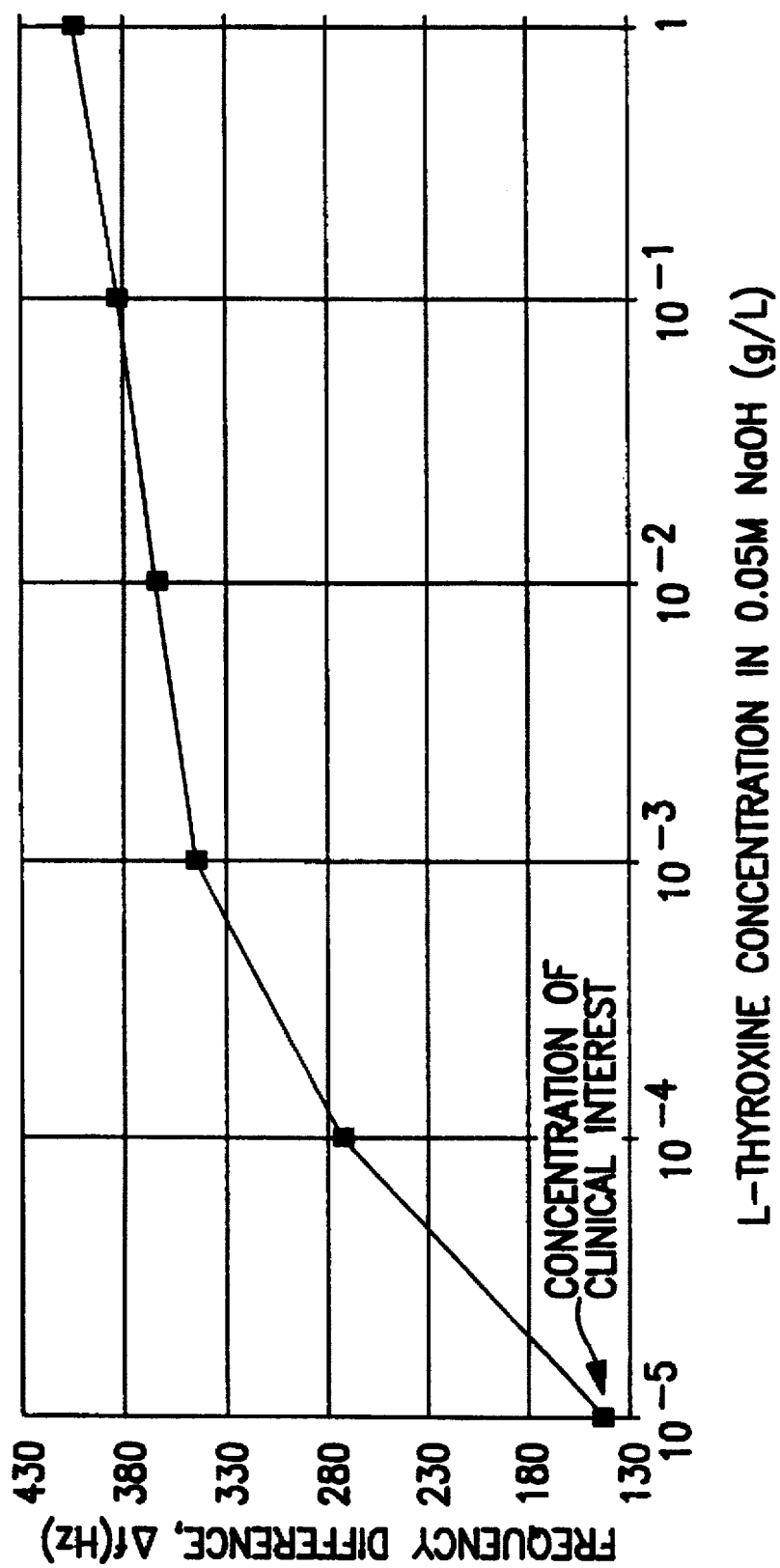
FIG. 9 depicts a plot of frequency difference vs. L-thyroxine concentration in NaOH.
Figure 10:
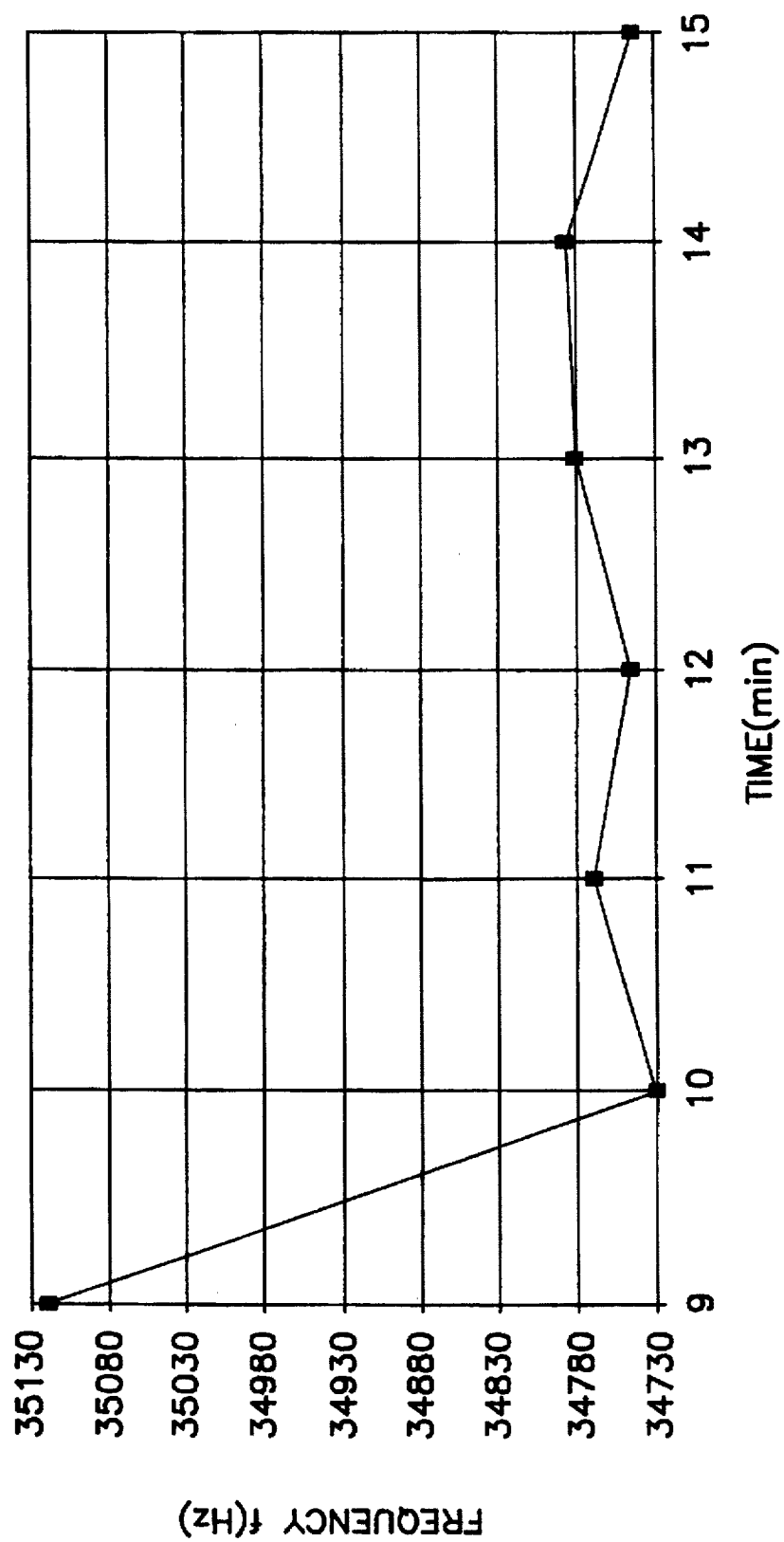
FIG. 10 depicts a plot of frequency vs. time for a 100,000 µg/dL concentration L-thyroxine solution.
Figure 11:
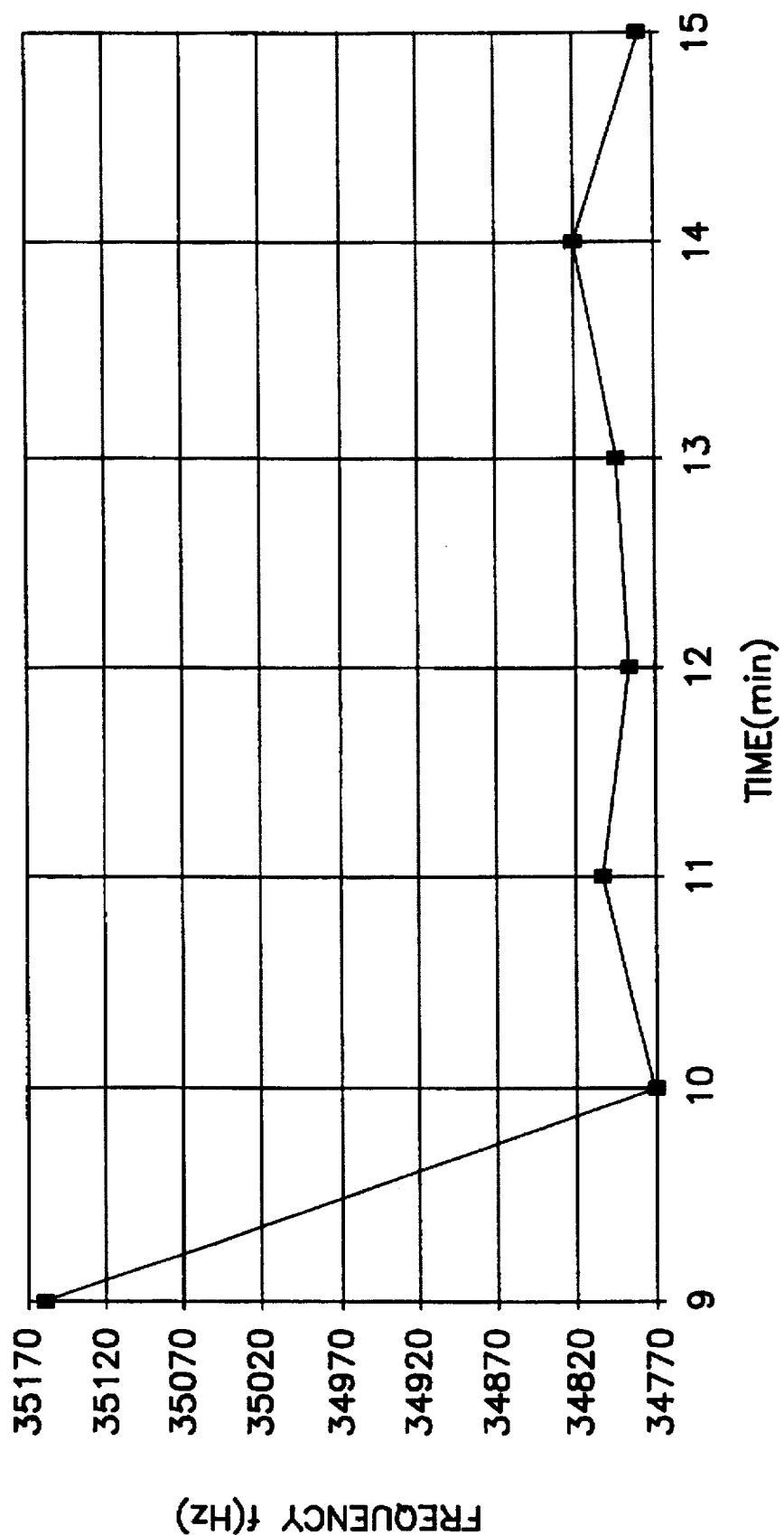
FIG. 11 depicts a plot of frequency vs. time for a 10,000 µg/dL concentration L-thyroxine solution.
Figure 12:
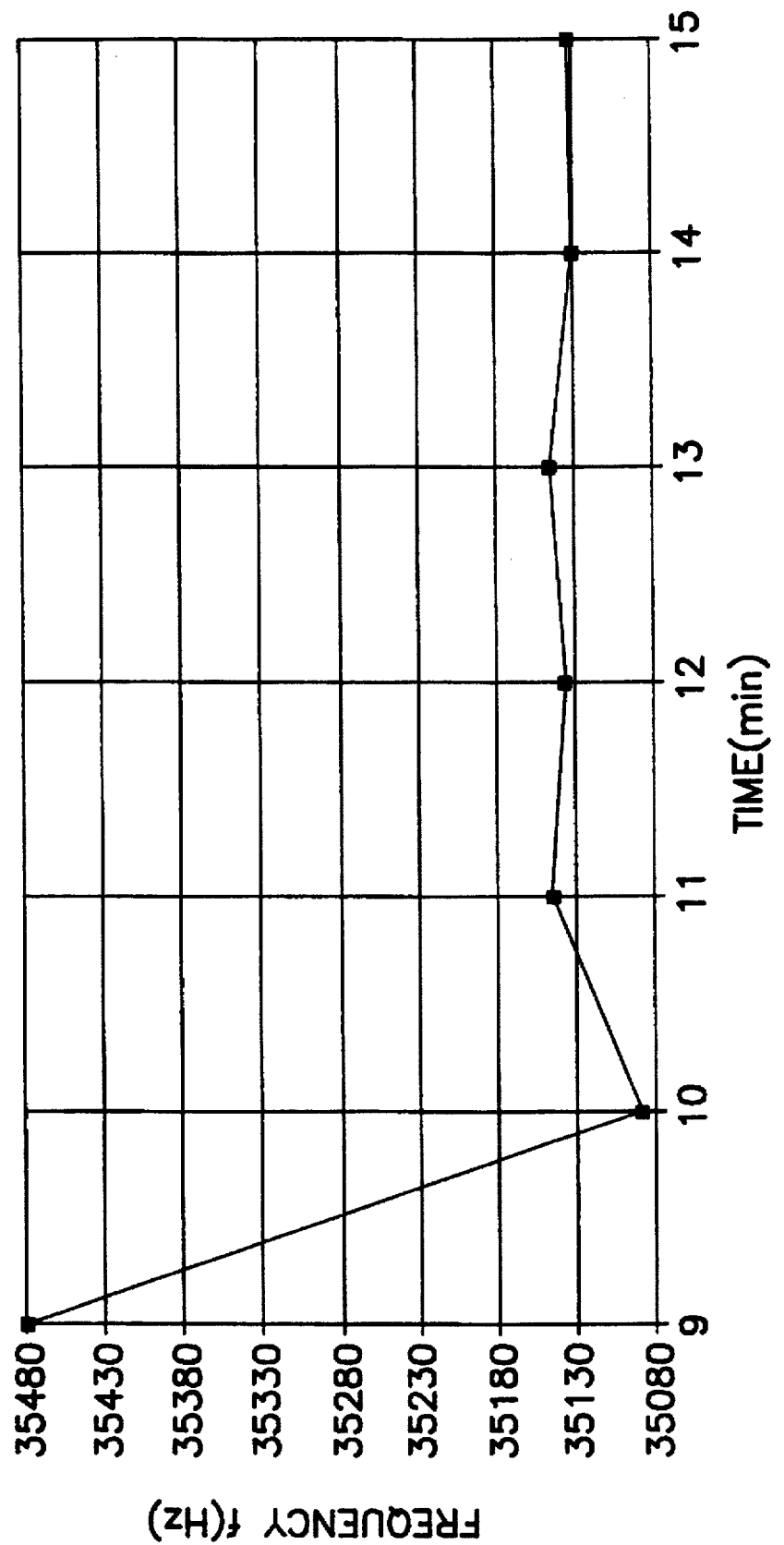
FIG. 12 depicts a plot of frequency vs. time for a 1000 µg/dL concentration L-thyroxine solution.
Figure 13:
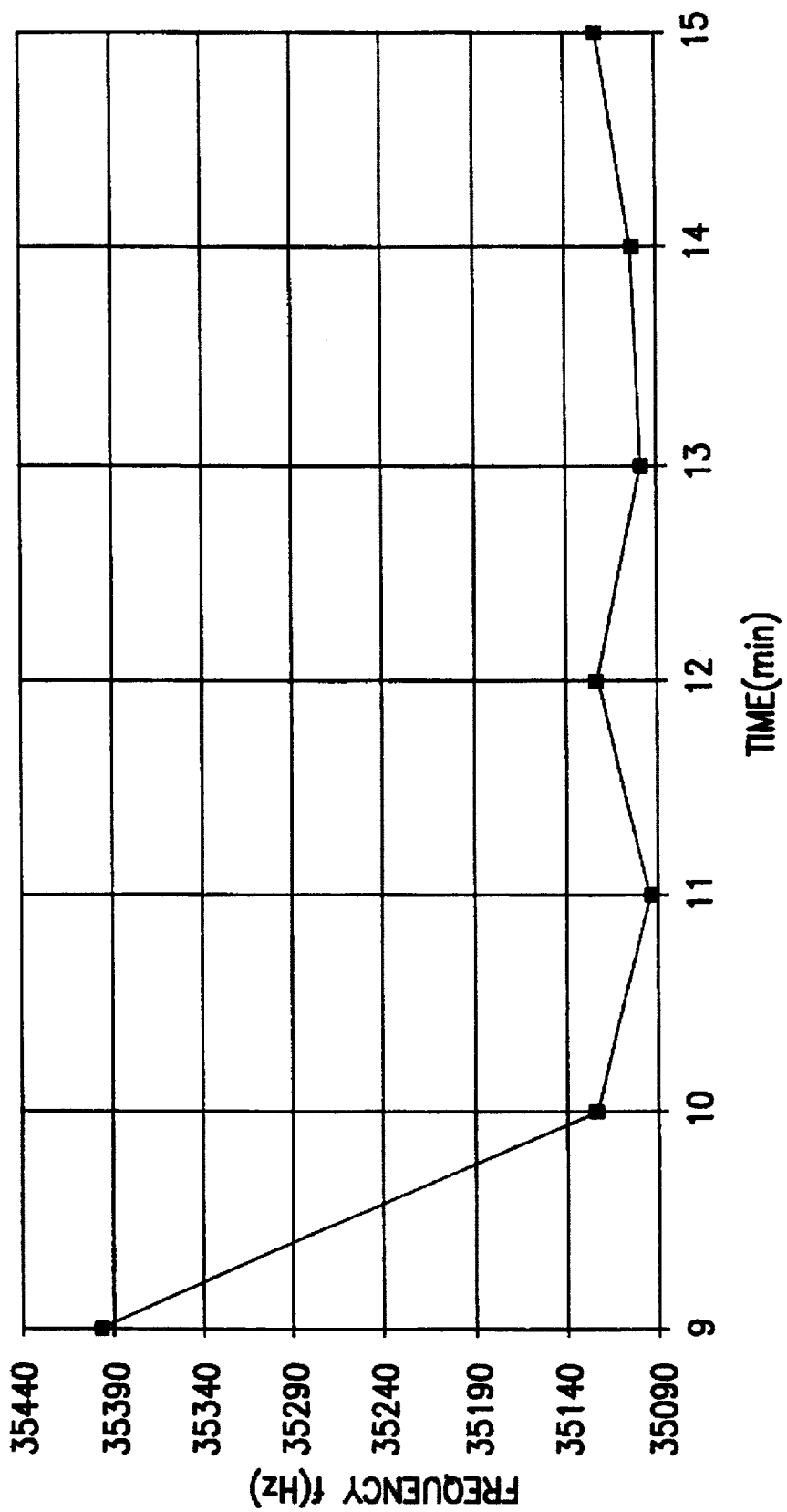
FIG. 13 depicts a plot of frequency vs. time for a 100 µg/dL concentration L-thyroxine solution.
Figure 14:
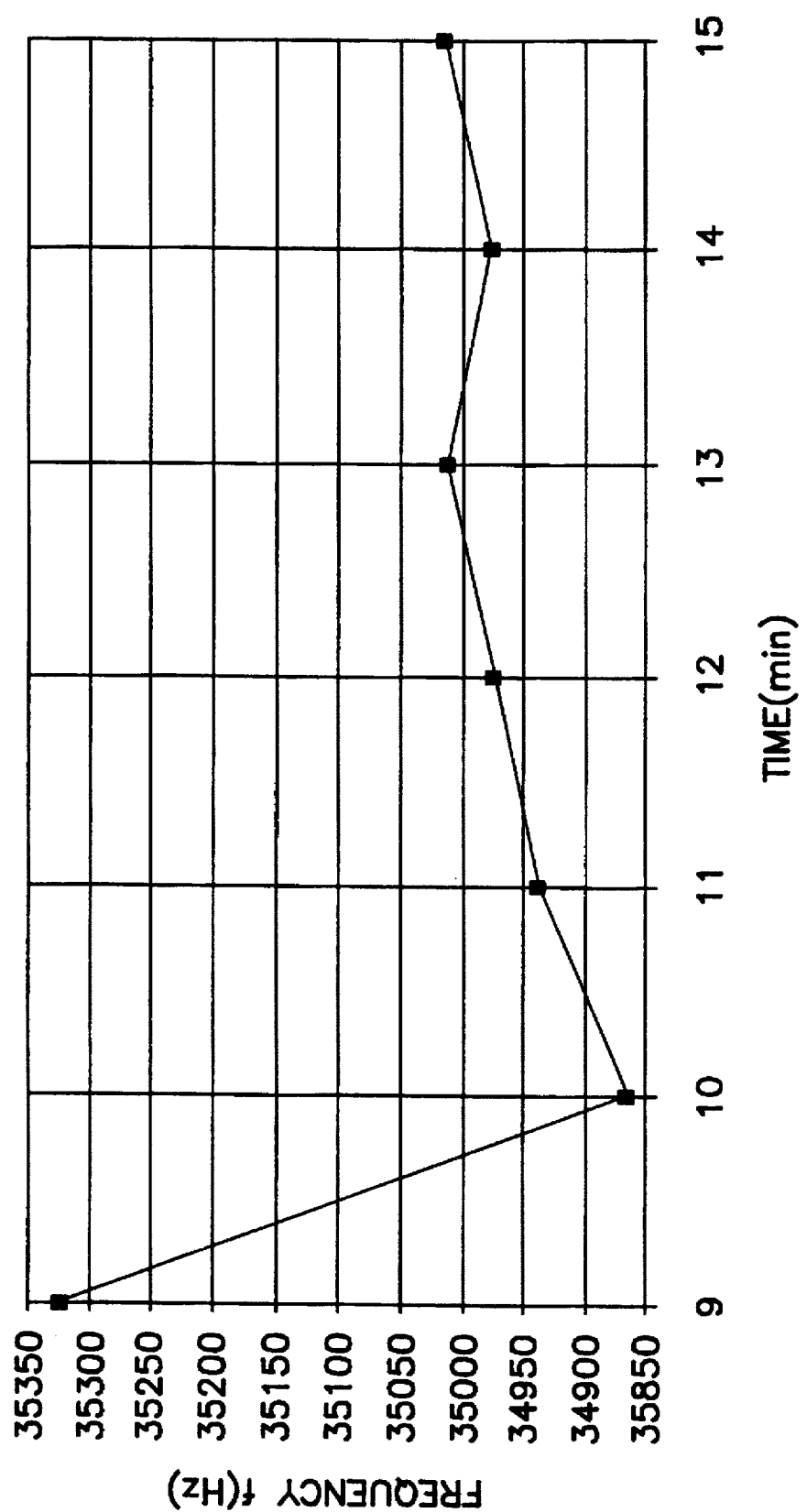
FIG. 14 depicts a plot of frequency vs. time for a 10 µg/dL concentration L-thyroxine solution.

The calibration curve generated from the data in Table 2 is graphically depicted in FIG. 7. Based upon the obtained results, the optimum coating concentration was determined to be at a 1:1000 dilution of the Anti-$T_4$ in the buffer. In addition, FIG. 8 depicts the trial run used to obtain the frequency difference for the 1:1000 dilution of Anti-$T_4$. It can be seen that the frequency change of highest magnitude occurs between time at 12 minutes and time at 14 minutes. This corresponds to the interval in which $T_4$, the antigen to the Anti-$T_4$, is added to the sensor. In addition, the frequency changes appeared to level off as the time interval approached 40 minutes. All measurements, except for those done on the standard addition to rat serum, were made using the frequency at 9 minutes minus the frequency at 14 minutes. A study of the time of antibody-antigen interaction stabilization, on the sensor, was performed as previously discussed. By performing trials of frequency difference versus time for the addition of $T_4$ to the sensor-coating system, it was determined that the region of greatest single-step change occurred within a runtime of fifteen minutes, as shown in FIG. 7.

EXAMPLE 6

L-Thyroxine Calibration—Range of Applicability

To determine the concentrations of $T_4$ that would yield appropriate readings using the sensor, a series of dilutions were made of the $T_4$ in 0.05M NaOH. They were in a range from 100,000 micrograms per deciliter (1 g/L) to 10 micrograms per deciliter ($10^{31.5}$ g/L).

FIG. 8 graphically illustrates the curve generated from frequency differences as functions of concentration changes.

The invention as applied to thyroxine detection and measurement is desired for use in a clinical region of interest in the range of micrograms per deciliter. The correlation coefficient calculated for the linear regression of frequency change versus $T_4$ concentration at high concentrations (i.e. 1 g/L) was 0.998. The correlation coefficient calculated for the thyroxine concentration of clinical interest (i.e. 10 mg/dL) was 0.996.

In order to determine whether or not these values were acceptable to federal agencies and clinical laboratories, various sources were contacted. The U.S. Food and Drug Administration (FDA), Clinical Devices Section, was contacted, and the guidelines that they have as of 1994 called for correlation coefficient values for RIA thyroxine assays to be at a minimum of 0.900. This was a low value, statistically speaking, therefore several clinical laboratories were contacted in order to find out what were typically accepted correlation coefficient values.

Abbott Laboratories gave a value of 0.987 as their acceptable minimum; Sigma Biomedicals gave a value of 0.920 as their acceptable minimum; and Diagnostic Products Corporation gave a value of 0.995 as an acceptable minimum.

The correlation coefficient values of the present invention for the addition of thyroxine to a blood matrix gave values that exceeded the minimum accepted by both the FDA and clinical laboratories.

FIGS. 9–14 depict the trial results of frequency difference versus time for the thyroxine concentrations used to generate the $T_4$ characterization curve (i.e. FIG. 8).

EXAMPLE 7

Standard Addition of L-thyroxine to Rat Serum

Figure 15:
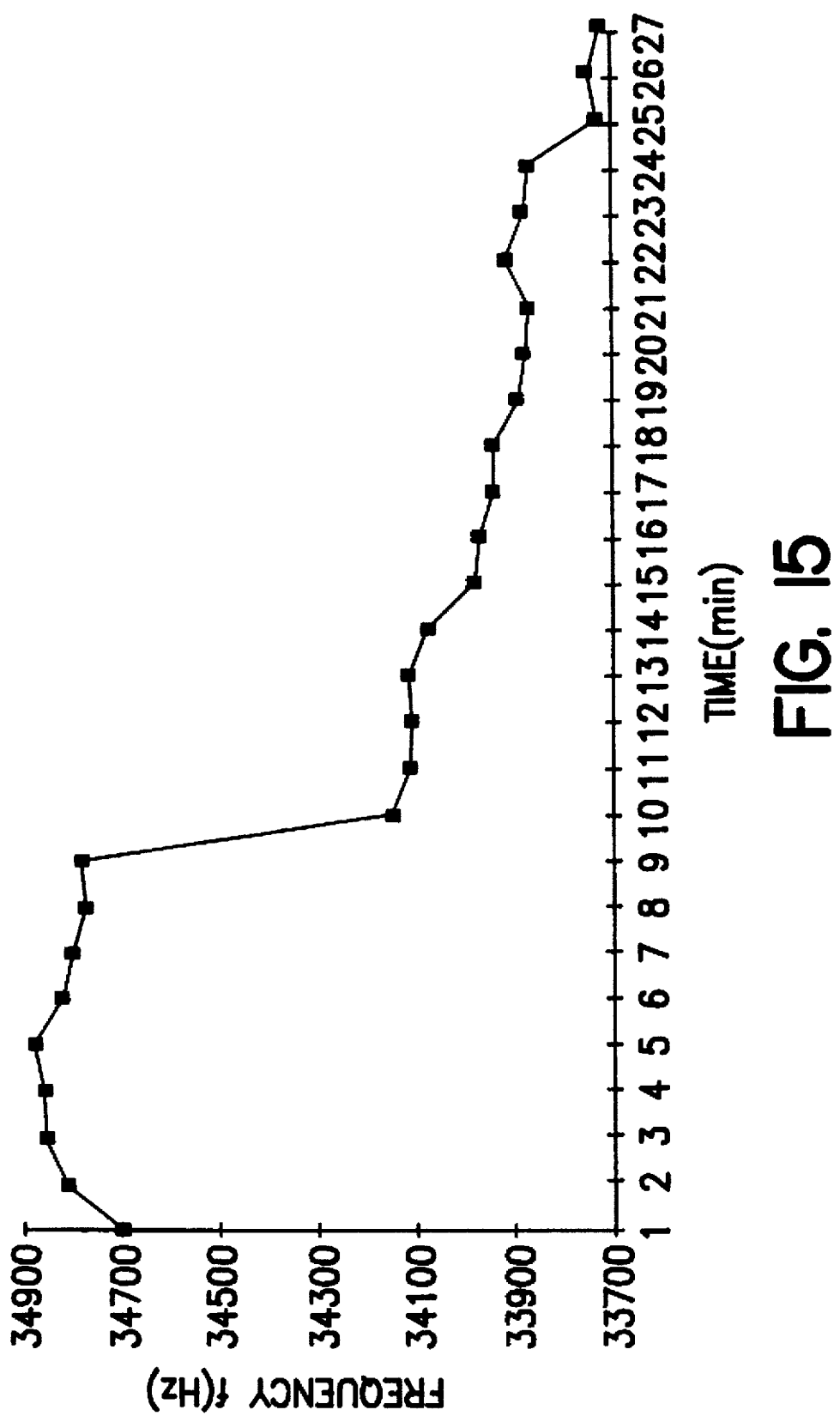
FIG. 15 depicts a standard addition curve obtained for the addition of L-thyroxyine to rat serum.
Figure 16:
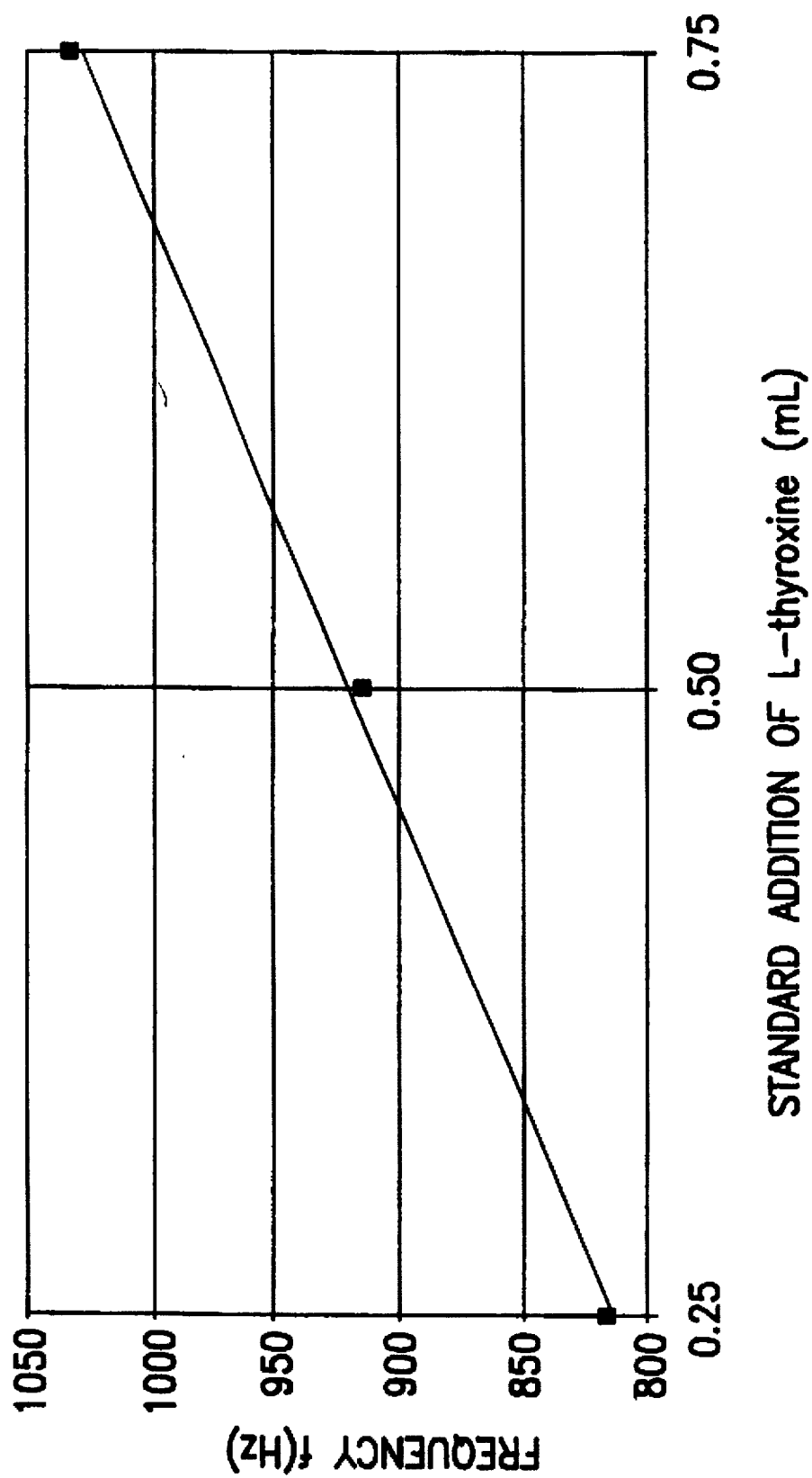
FIG. 16 depicts a linear regression curve obtained for the standard addition of L-thyroxine to rat serum.

The data obtained from standard addition of thyroxine to rat serum elucidate the applicability of this invention for useful clinical means, such as $T_4$ detection in human blood. As was stated earlier, the range of clinical interest for thyroxine analysis is between 0.5–25 µg/dL. The thyroxine concentration of the rat serum sample used was experimentally determined to be 0.81 µg/dL, using a standard $T_4$ concentration of 10 µg/dL for the additions. FIG. 15 depicts the standard addition curve generated using a $T_4$ standard solution concentration of 10 µg/dL for the measurement of a blood serum sample that was 0.81 µg/dL in $T_4$. FIG. 16 shows the linear regression performed on the data obtained from standard addition.

Determination of the unknown $T_4$ concentration in the rat serum sample was accomplished by a standard addition calculation. The system chosen was continuous variation of standard (thyroxine addition aliquots) at constant total volume. The equation used to calculate the concentration of thyroxine in the rat serum was $$C_x = bV_sC_s/mV_x$$

where $C_x$ is the concentration of the rat serum, m is the slope and b is the intercept obtained from a linear regression performed on the standard addition curve; $V_s$ is the volume of the added aliquot, $C_s$ is the concentration of the added thyroxine aliquot, and $V_x$ is the volume of the rat serum. Table 3 lists the values obtained from the linear regression performed and the data needed to calculate $C_x$ the concentration of $T_4$ in the rat serum sample.

TABLE 3

| STANDARD ADDITION INFORMATION | |
|---|---|
| PARAMETER | VALUE |
| b | 704 Hz |
| m | 434 Hz/mL |
| $V_s$ | 0.25 mL |
| $C_s$ | 10 µg/dL |
| $V_x$ | 5 mL |
| $C_x$ | 0.81 µg/dL |

Since the linear regression data was more than acceptable having a correlation coefficient of 0.996, the corresponding calculations for the concentration of thyroxine in rat serum were likewise reliable and determined to be 0.81 mg/dL.

Although this invention has been illustrated by reference to specific embodiments, it will be apparent to those skilled in the art that various changes and modifications may be made which clearly fall within the scope of this invention.

The invention claimed is:

1. A quartz crystal microbalance chemical sensor comprising:
   (a) a crystal detector oscillator having a resonant frequency and capable of providing a measurement signal based upon the resonant frequency of the detector oscillator, the crystal detector oscillator having a first crystal side for directly contacting a solution, and a second crystal side isolated from contacting the solution;
   (b) a first electrode integral to the first crystal side, the first electrode having an inner and outer perimeter defining an outer portion of the first crystal side which is exterior to the outer perimeter of the first electrode and an inner portion of the first crystal side which is interior to the inner perimeter of the first electrode; and
   (c) a second electrode integral to the second crystal side.

2. The sensor of claim 1, wherein the sensor measures the concentration of predetermined chemical species in solution with the first crystal side having a coating applied thereto, and a change in sensor mass relating to degradation of the coating in response to the presence of the chemical species is measured.

3. The sensor of claim 2, wherein the coated first crystal side is contacted with a solution containing the predetermined chemical species.

4. The sensor of claim 1, wherein the crystal detector oscillator is a quartz crystal.

5. The sensor of claim 4, wherein the crystal detector oscillator is an AT-cut quartz crystal.

6. The sensor of claim 1, wherein the first electrode is gold, silver, nickel, chromium or tantalum, and the second electrode is gold, silver, nickel, chromium or tantalum.

7. The sensor of claim 1, wherein the first and second electrodes are vacuum deposited on the first and second crystal sides, respectively.

8. The sensor of claim 1, wherein the sensor additionally comprises means operatively coupled to the crystal detector oscillator for conveying the measurement signal for signal processing.

9. The sensor of claim 1, wherein the first electrode is ring-shaped.

10. The sensor of claim 1, wherein the first crystal side is contacted with a solution containing a predetermined chemical species-specific complementary material prior to contacting the first crystal side with a predetermined chemical species-containing solution.

11. The sensor of claim 10, wherein the complementary material is an antibody.

12. The sensor of claim 11, wherein the predetermined chemical species is thyroxine and the antibody is anti-thyroxine.

13. The sensor of claim 11, wherein the predetermined chemical species is calcitonin and the antibody is anti-calcitonin.

14. The sensor of claim 1, wherein the solution is human blood.

15. A method for detecting the concentration of predetermined chemical species in solution, the method consisting essentially of:
   (a) providing a quartz crystal microbalance chemical sensor which comprises (i) a crystal detector oscillator having a resonant frequency and capable of providing a measurement signal based upon the resonant frequency of the detector oscillator, the crystal detector oscillator having a first crystal side for contacting the species-containing solution, and a second crystal side isolated from contacting the species-containing solution, (ii) a first electrode integral to the first crystal side, the first electrode having an inner and outer perimeter defining an outer portion of the first crystal side which is exterior to the outer perimeter of the first electrode and an inner portion of the first crystal side which is interior to the inner perimeter of the first electrode, and (iii) a second electrode integral to the second crystal side;
   (b) contacting the first crystal side with a solution containing a predetermined species-specific complementary material to the predetermined chemical species, wherein the species-specific complementary material is adsorbed onto the first crystal side;
   (c) measuring the resonant frequency of the crystal detector oscillator after contacting with the solution containing the complementary material;
   (d) contacting the first crystal side with a solution containing the predetermined chemical species, thereby causing binding of the predetermined chemical species to the complementary material-adsorbed first crystal side;
   (e) measuring the resonant frequency of the crystal detector oscillator after contacting the first crystal side with the species-containing solution; and
   (f) comparing the difference in resonant frequencies measured in steps (c) and (e) to determine the concentration of the species in the species-containing solution.

16. The method of claim 15, further comprising the steps of providing a reference oscillator having a reference resonant frequency, comparing the difference between the resonant frequency measured in step (c) and the reference resonant frequency to obtain a first normalized resonant frequency, comparing the difference between the resonant frequency measured in step (e) and the reference resonant frequency to obtain a second normalized resonant frequency, and comparing the difference between the first and second normalized resonant frequencies to determine the concentration of the chemical species in the species-containing solution.

17. The method of claim 15, wherein the complementary material is an antibody.

18. The method of claim 17, wherein the predetermined chemical species is thyroxine and the antibody is anti-thyroxine.

19. The method of claim 17, wherein the predetermined chemical species is calcitonin and the antibody is anti-calcitonin.

20. The method of claim 15, wherein the species-containing solution is human blood.

21. The method of claim 15, further comprising after step (f) the step of contacting the first crystal side with a cleaning solution to remove the species and complementary material from the surface of the first crystal side and regenerate active sites on the surface of the first crystal side.

22. An apparatus comprising:

a quartz crystal microbalance chemical sensor which comprises (i) a crystal detector oscillator having a resonant frequency and capable of providing a measurement signal based upon the resonant frequency of the crystal detector oscillator, the crystal detector oscillator having a first crystal side for directly contacting a solution, and a second crystal side isolated from contacting the solution, (ii) a first electrode integral to the first crystal side, the first electrode having an inner and outer perimeter defining an outer portion of the first crystal side which is exterior to the outer perimeter of the first electrode and an inner portion of the first crystal side which is interior to the inner perimeter of the first electrode; and (iii) a second electrode integral to the second crystal side; and sensor detecting means operatively coupled to the sensor for detecting the resonant frequency of the crystal detector oscillator and providing a detector output signal representative of the crystal detector oscillator resonant frequency.

23. The apparatus of claim 22, further comprising:

display means operatively coupled to the sensor detecting means for displaying the detector output signal.

24. The apparatus of claim 22, further comprising:

a reference oscillator having a resonant frequency;

reference detecting means operatively coupled to the reference oscillator for detecting the resonant frequency of the reference oscillator and providing a reference output signal representative of the reference oscillator resonant frequency; and signal comparison means operatively coupled to the sensor detecting means and the reference detecting means for comparing the difference between the detector output signal and the reference output signal and providing a difference output signal.

25. The apparatus of claim 24, further comprising:

display means operatively coupled to the signal comparison means for displaying the difference output signal.

26. The apparatus of claim 22, wherein the sensor measures the concentration of predetermined chemical species in solution with the first crystal side having a coating applied thereto, and a change in sensor mass relating to degradation of the coating in response to the presence of the chemical species is measured.

27. The apparatus of claim 26, wherein the coated first crystal side is contacted with a solution containing the predetermined chemical species.

28. A method for detecting the concentration of predetermined chemical species in solution, the method consisting essentially of:

(a) providing an apparatus which comprises a quartz crystal microbalance chemical sensor which comprises (i) a crystal detector oscillator having a resonant frequency and capable of providing a measurement signal based upon the resonant frequency of the crystal detector oscillator, the crystal detector oscillator having a first crystal side for contacting the species-containing solution, and a second crystal side isolated from contacting the species-containing solution, (ii) a first electrode integral to the first crystal side, the first electrode having an inner and outer perimeter defining, an outer portion of the first crystal side which is exterior to the outer perimeter of the first electrode and an inner portion of the first crystal side which is interior to the inner perimeter of the first electrode; and (iii) a second electrode integral to the second crystal side; and sensor detecting means operatively coupled to the sensor for detecting the resonant frequency of the crystal detector oscillator and providing a detector output signal representative of the crystal detector oscillator resonant frequency;

(b) contacting the first crystal side with a solution containing a predetermined species-specific complementary material to the predetermined chemical species, wherein the species-specific complementary material is adsorbed onto the first crystal side;

(c) measuring the resonant frequency of the crystal detector oscillator after contacting with the solution containing the complementary material;

(d) contacting the first crystal side with a solution containing the predetermined chemical species, thereby causing binding of the predetermined chemical species to the complementary material-adsorbed first crystal side;

(e) measuring the resonant frequency of the crystal detector oscillator after contacting the first crystal side with the species-containing solution; and (f) comparing the difference in resonant frequencies measured in steps (c) and (e) to determine the concentration of the species in the species-containing solution.

29. The method of claim 28, further comprising:

providing a reference oscillator;

providing reference detecting means operatively coupled to the reference oscillator for detecting the resonant frequency of the reference oscillator and providing a reference output signal representative of the reference oscillator resonant frequency;

providing signal comparison means operatively coupled to the sensor detecting means and the reference detecting means for comparing the difference between the detector output signal and the reference output signal and providing a difference output signal;

comparing the difference between the resonant frequency measured in step (c) and the reference resonant frequency to obtain a first normalized resonant frequency, comparing the difference between the resonant frequency measured in step (e) and the reference resonant frequency to obtain a second normalized resonant frequency; and comparing the difference between the first and second normalized resonant frequencies to determine the concentration of the chemical species in the species-containing solution.

30. A quartz crystal microbalance chemical sensor for measuring the concentration of predetermined chemical species in solution by measuring a change in sensor mass relating to interaction of a surface of the sensor with a solution, the sensor comprising:

(a) a crystal detector oscillator having a resonant frequency and capable of providing a measurement signal based upon the resonant frequency of the detector oscillator, the crystal detector oscillator having a first crystal side for contacting the solution, and a second crystal side isolated from contacting the solution;

(b) a first electrode integral to the first crystal side, the first electrode having an inner and outer perimeter defining an outer portion of the first crystal side which is exterior to the outer perimeter of the first electrode and an inner portion of the first crystal side which is interior to the inner perimeter of the first electrode; and (c) a second electrode integral to the second crystal side, wherein the first crystal side has a coating applied thereto and a change in sensor mass relating to interaction of the coating with the predetermined chemical species is measured.

31. The sensor of claim 30, wherein the coated first crystal side is contacted with a solution containing the predetermined chemical species.

32. The sensor of claim 30, wherein the crystal detector oscillator is a quartz crystal.

33. The sensor of claim 30, wherein the crystal detector oscillator is an AT-cut quartz crystal.

34. The sensor of claim 30, wherein the first electrode is gold, silver, nickel, chromium or tantalum, and the second electrode is gold, silver, nickel, chromium or tantalum.

35. The sensor of claim 30, wherein the first and second electrodes are vacuum deposited on the first and second crystal sides, respectively.

36. The sensor of claim 30, wherein the sensor additionally comprises means operatively coupled to the crystal detector oscillator for conveying the measurement signal for signal processing.

37. The sensor of claim 30, wherein the first electrode is ring-shaped.

38. The sensor of claim 30, wherein the first crystal side is coated by contacting the first crystal side with a solution containing a predetermined species-specific complementary material prior to contacting the first crystal side with the species-containing solution.

39. The sensor of claim 38, wherein the complementary material is an antibody.

40. The sensor of claim 39, wherein the predetermined chemical species is thyroxine and the antibody is anti-thyroxine.

41. The sensor of claim 38, wherein the predetermined chemical species is calcitonin and the antibody is anti-calcitonin.

42. The sensor of claim 30, wherein the species-containing solution is human blood.

43. A method for detecting the concentration of predetermined chemical species in solution by measuring a change in sensor mass relating to interaction of a surface of the sensor with a solution, the method consisting essentially of:

(a) providing a quartz crystal microbalance chemical sensor which comprises (i) a crystal detector oscillator having a resonant frequency and capable of providing a measurement signal based upon the resonant frequency of the detector oscillator, the crystal detector oscillator having a first crystal side for contacting the species-containing solution, and a second crystal side isolated from contacting the species-containing solution, (ii) a first electrode integral to the first crystal side, the first electrode having an inner and outer perimeter defining an outer portion of the first crystal side which is exterior to the outer perimeter of the first electrode and an inner portion of the first crystal side which is interior to the inner perimeter of the first electrode, and (iii) a second electrode integral to the second crystal side;

(b) applying a coating to the first crystal side by contacting the first crystal side with a solution containing a predetermined species-specific complementary material to the predetermined chemical species;

(c) measuring the resonant frequency of the crystal detector oscillator after contacting with the solution containing the complementary material;

(d) contacting the first crystal side with a solution containing the predetermined chemical species;

(e) measuring the resonant frequency of the crystal detector oscillator after contacting the first crystal side with the species-containing solution; and (f) comparing the difference in resonant frequencies measured in steps (c) and (e) to determine the concentration of the species in the species-containing solution.

44. The method of claim 43, further comprising the steps of providing a reference oscillator having a reference resonant frequency, comparing the difference between the resonant frequency measured in step (c) and the reference resonant frequency to obtain a first normalized resonant frequency, comparing the difference between the resonant frequency measured in step (e) and the reference resonant frequency to obtain a second normalized resonant frequency, and comparing the difference between the first and second normalized resonant frequencies to determine the concentration of the chemical species in the species-containing solution.

45. The method of claim 43, wherein the complementary material is an antibody.

46. The method of claim 45, wherein the predetermined chemical species is thyroxine and the antibody is anti-thyroxine.

47. The method of claim 45, wherein the predetermined chemical species is calcitonin and the antibody is anti-calcitonin.

48. The method of claim 43, wherein the species-containing solution is human blood.

49. The method of claim 43, further comprising after step (f) the step of contacting the first crystal side with a cleaning solution to remove the species and complementary material from the surface of the first crystal side and regenerate active sites on the surface of the first crystal side.

50. An apparatus for measuring the concentration of predetermined chemical species in solution comprising:

a quartz crystal microbalance chemical sensor which comprises (i) a crystal detector oscillator having a resonant frequency and capable of providing a measurement signal based upon the resonant frequency of the crystal detector oscillator, the crystal detector oscillator having a first crystal side for contacting a solution, and a second crystal side isolated from contacting the solution, (ii) a first electrode integral to the first crystal side, the first electrode having an inner and outer perimeter defining an outer portion of the first crystal side which is exterior to the outer perimeter of the first electrode and an inner portion of the first crystal side which is interior to the inner perimeter of the first electrode; and (iii) a second electrode integral to the second crystal side; and sensor detecting means operatively coupled to the sensor for detecting the resonant frequency of the crystal detector oscillator and providing a detector output signal representative of the crystal detector oscillator resonant frequency, wherein the first crystal side has a coating applied thereto, and a change in sensor mass relating to interaction of the coating with the predetermined chemical species is measured.

51. The apparatus of claim 50, wherein the coated first crystal side is contacted with a solution containing the predetermined chemical species.

52. The apparatus of claim 50, further comprising:

display means operatively coupled to the sensor detecting means for displaying the detector output signal.

53. The apparatus of claim 50, further comprising:

a reference oscillator;

reference detecting means operatively coupled to the reference oscillator for detecting the resonant frequency of the reference oscillator and providing a reference output signal representative of the reference oscillator resonant frequency; and signal comparison means operatively coupled to the sensor detecting means and the reference detecting means for comparing the difference between the detector output signal and the reference output signal and providing a difference output signal.

54. The apparatus of claim 53, further comprising:

display means operatively coupled to the signal comparison means for displaying the difference output signal.

55. A method for detecting the concentration of predetermined chemical species in solution by measuring a change in sensor mass relating to interaction of a surface of the sensor with a solution, the method consisting essentially of:

(a) providing an apparatus which comprises a quartz crystal microbalance chemical sensor which comprises (i) a crystal detector oscillator having a resonant frequency and capable of providing a measurement signal based upon the resonant frequency of the crystal detector oscillator, the crystal detector oscillator having a first crystal side for contacting the species-containing solution, and a second crystal side isolated from contacting the species-containing solution, (ii) a first electrode integral to the first crystal side, the first electrode having an inner and outer perimeter defining, an outer portion of the first crystal side which is exterior to the outer perimeter of the first electrode and an inner portion of the first crystal side which is interior to the inner perimeter of the first electrode; and (iii) a second electrode integral to the second crystal side; and sensor detecting means operatively coupled to the sensor for detecting the resonant frequency of the crystal detector oscillator and providing a detector output signal representative of the crystal detector oscillator resonant frequency;

(b) applying a coating to the first crystal side by contacting the first crystal side with a solution containing a predetermined species-specific complementary material to the predetermined chemical species;

(c) measuring the resonant frequency of the crystal detector oscillator after contacting with the solution containing the complementary material;

(d) contacting the first crystal side with a solution containing the predetermined chemical species;

(e) measuring the resonant frequency of the crystal detector oscillator after contacting the first crystal side with the species-containing solution; and (f) comparing the difference in resonant frequencies measured in steps (c) and (e) to determine the concentration of the species in the species-containing solution.

56. The method of claim 55, further comprising:

providing a reference oscillator;

providing reference detecting means operatively coupled to the reference oscillator for detecting the resonant frequency of the reference oscillator and providing a reference output signal representative of the reference oscillator resonant frequency;

providing signal comparison means operatively coupled to the sensor detecting means and the reference detecting means for comparing the difference between the detector output signal and the reference output signal and providing a difference output signal;

comparing the difference between the resonant frequency measured in step (c) and the reference resonant frequency to obtain a first normalized resonant frequency, comparing the difference between the resonant frequency measured in step (e) and the reference resonant frequency to obtain a second normalized resonant frequency; and comparing the difference between the first and second normalized resonant frequencies to determine the concentration of the chemical species in the species-containing solution.

\* \* \* \* \*

UNITED STATES PATENT AND TRADEMARK OFFICE
CERTIFICATE OF CORRECTION

PATENT NO. : 5,705,399

DATED : January 6, 1998

INVENTOR(S) : Rebecca A. LaRue

It is certified that error appears in the above-identified patent and that said Letters Patent is hereby corrected as shown below:

Col. 8, line 15, "L-thyroxyine" should read --L-thyroxine";

Col. 12, line 6, "complementary, " should read --complementary--;

Col. 19, line 65, "$10^{31}$ 5 g/L)" should read --($10^{-5}$ g/L)--;

Col. 24, line 3, "defining, an" should read --defining an--;

Col. 25, line 49, "Of" should read --of--;

Col. 27, line 37, "defining, an" should read --defining an--.

Signed and Sealed this

Twenty-sixth Day of May, 1998

Attest:

BRUCE LEHMAN

Attesting Officer

Commissioner of Patents and Trademarks